(12) United States Patent
Shaikh et al.

(10) Patent No.: US 9,834,497 B2
(45) Date of Patent: Dec. 5, 2017

(54) SYSTEMS AND METHODS FOR PRODUCING PROPYLENE

(71) Applicant: Saudi Arabian Oil Company, Dhahran (SA)

(72) Inventors: Sohel Shaikh, Dhahran (SA); Aqil Jamal, Dhahran (SA); Zhonglin Zhang, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/191,009

(22) Filed: Jun. 23, 2016

(65) Prior Publication Data

US 2017/0001928 A1    Jan. 5, 2017

Related U.S. Application Data

(60) Provisional application No. 62/188,068, filed on Jul. 2, 2015.

(51) Int. Cl.
*C07C 6/04* (2006.01)
*C07C 4/02* (2006.01)
*C07C 4/06* (2006.01)

(52) U.S. Cl.
CPC ............... *C07C 6/04* (2013.01); *C07C 4/06* (2013.01); *C07C 2521/08* (2013.01); *C07C 2523/30* (2013.01); *C07C 2529/40* (2013.01)

(58) Field of Classification Search
CPC .................................... C07C 6/04; C07C 4/02
(Continued)

(56) References Cited

U.S. PATENT DOCUMENTS 3,586,731 A    6/1971  Heckelsberg
4,024,201 A    5/1977  Takahashi
(Continued)

FOREIGN PATENT DOCUMENTS

CN    104370676 A    2/2015
EP       304515 B1   12/1991
(Continued)

OTHER PUBLICATIONS

International Search Report and Written Opinion dated Sep. 27, 2016 pertaining to International Application No. PCT/US2016/038967.

(Continued)

*Primary Examiner* — Thuan D Dang
(74) *Attorney, Agent, or Firm* — Dinsmore & Shohl LLP

(57) ABSTRACT

According to one or more embodiments described herein, a process for producing propylene, the process comprising at least partially metathesizing a first portion of a first stream to form a first metathesis-reaction product, at least partially cracking the first metathesis-reaction product to form a cracking-reaction product, the cracking reaction product comprising propylene and ethylene, at least partially separating ethylene from at least the cracking reaction product to form a first recycle stream, combining the first recycle stream with a second portion of the first stream to a form a mixed stream, and at least partially metathesizing the mixed stream to from a second metathesis-reaction product. In embodiments, the second metathesis-reaction product may comprise propylene, the first stream may comprise butene, and the first recycle stream may comprise ethylene.

23 Claims, 4 Drawing Sheets

(58) Field of Classification Search
USPC .......................... 585/324, 650, 643, 645
See application file for complete search history.

(56) References Cited

U.S. PATENT DOCUMENTS

| | | | |
|---|---|---|---|
| 4,071,471 | A | 1/1978 | Banks |
| 5,026,935 | A | 6/1991 | Leyshon et al. |
| 5,026,936 | A | 6/1991 | Leyshon et al. |
| 6,207,115 | B1 | 3/2001 | Chodorge et al. |
| 6,538,168 | B1 | 3/2003 | Schwab et al. |
| 6,586,649 | B1 | 7/2003 | Botha et al. |
| 6,646,172 | B1 | 11/2003 | Schwab et al. |
| 6,777,582 | B2 | 8/2004 | Gartside et al. |
| 7,214,841 | B2 | 5/2007 | Gartside et al. |
| 7,754,647 | B2 | 7/2010 | Schubert et al. |
| 7,754,934 | B2 | 7/2010 | Tsunoda et al. |
| 8,299,313 | B2 | 10/2012 | Takai et al. |
| 8,440,874 | B2 | 5/2013 | Ramachandran et al. |
| 8,586,813 | B2 | 11/2013 | Ramachandran et al. |
| 8,722,568 | B2 | 5/2014 | Popp et al. |
| 2004/0254411 | A1 | 12/2004 | Steinbrenner et al. |
| 2005/0014981 | A1* | 1/2005 | Gartside ................. C07C 6/04 585/324 |
| 2006/0293548 | A1 | 12/2006 | Spamer et al. |
| 2007/0038010 | A1 | 2/2007 | Xie et al. |
| 2007/0225478 | A1 | 9/2007 | Querci et al. |
| 2009/0170692 | A1 | 7/2009 | Ying et al. |
| 2011/0021858 | A1 | 1/2011 | Ramachandran et al. |
| 2011/0152595 | A1 | 6/2011 | Takai et al. |
| 2011/0196185 | A1 | 8/2011 | Krawczyk et al. |
| 2012/0108864 | A1 | 5/2012 | Gartside et al. |
| 2012/0283090 | A1 | 11/2012 | Popp et al. |
| 2012/0289617 | A1 | 11/2012 | Wang et al. |

FOREIGN PATENT DOCUMENTS

| | | |
|---|---|---|
| WO | 9929805 A1 | 6/1999 |
| WO | 2006089957 A1 | 8/2006 |
| WO | 2009117128 A1 | 9/2009 |
| WO | 2010019595 A2 | 2/2010 |
| WO | 2011136983 A1 | 11/2011 |
| WO | 2015055594 A1 | 4/2015 |

OTHER PUBLICATIONS

International Search Report pertaining to PCT/US2016/039025, filed Jun. 23, 2016, 6 pages.
Written Opinion pertaining to PCT/US2016/039025, filed Jun. 23, 2016, 5 pages.
Bin Hu, et al., Highly Active Doped Mesoporous KIT-6 Catalysts for Metathesis of 1-Butene and Ethene to Propene: The Influence of Neighboring Environment of W Species, The Journal of Physical Chemistry, ACS Publication, 2013 American Chemical Society, pp. 26385-26395, USA.
Ruihua Gao, et al., High-activity, single-site mesoporous WO3-MCF materials for the catalytic epoxidation of cycloocta-1,5-diene with aqueous hydrogen peroxide, Journal of Catalysis, 256, 2008, pp. 259-267, China.
H. Balcar, et al., Mesoporous molecular sieves as advanced supports for olefin metathesis catalysts, Coordination Chemistry Reviews 257, 2013, pp. 3107-3124, Czech Republic.
Daniell et al., Enhanced Surface Acidity in Mixed Alumina-Silicas: A Low-Temperature FTIR Study:, 2000, 196, 247-260, Elsevier.
International Search Report and Written Opinion dated Sep. 14, 2016 pertaining to International Application No. PCT/US2016/039013.
Kumar et al., Performance of Nano Crystalline H-ZSM-5 As Additive in FCC Catalyst: A Review, IJRET: International Journal of Research in Engineering and Technology, May 2014, vol. 3, pp. 481-485.
International Search Report and Written Opinion dated Sep. 14, 2016 pertaining to International Application No. PCT/US2016/039012.
Arudra et al., "Silicalite-1 as Efficient Catalyst for Production of Propene from 1-Butene", ACS Catalysis, 2014, 4205-4212, 4, American Chemical Society.
Awayssa et al., "Modified HZSM-5 as FCC Additive for Enhancing Light Olefins Yield from Catalytic Cracking of VGO", Applied Catalysis A: General, 2014, 172-183, 477.
Barrett et al., "The Determination of Pore Volume and Area Distributions in Porous Substances. I. Computations from Nitrogen Isotherms", J. Am. Chem. Soc., 1951, 373-380, 73(1).
Beck et al., "A New Family of Mesoporous Molecular Sieves Prepared with Liquid Crystal Templates", J. Am. Chem. Soc., 1992, 10834-10843, 114, American Chemical Society.
Bhuiyan et al., "Kinetics Modelling of 2-Butene Metathesis Over Tungsten Oxide Containing Mesoporous Silica Catalyst", The Canadian Journal of Chemical Engineering, 2014, 1271-1282. 92.
Bhuiyan et al., "Metathesis of 2-Butene to Propylene over W-Mesoporous Molecular Sieves: A Comparative Study Between Tungsten Containing MCM-41 and SBA-15", Applied Catalysis A: General, 2013, 224-234, 467, Elsevier B.V.
Do et al., "Zeolite Nanoclusters Coated onto the Mesopore Walls of SBA-15", J. Am. Chem. Soc., 2004, 14324-14325, 126, American Chemical Society.
Jermy et al., "Utilization of ZSM-5/MCM-41 Composite as FCC Catalyst Additive for Enhancing Propylene Yield from VGO Cracking", J. Porous Mater, 2012, 499-509, 19, Springer.
Lwin et al., "Olefin Metathesis by Supported Metal Oxide Catalysts", ACS Catalysis, 2014, 2505-2520, 4, American Chemical Society.
Wang et al., Synthesis and Structure of Silicalite-1/SBA-15 Composites Prepared by Carbon Templating and Crystallization, Journal of Materials Chemistry, 2007,4265-4273,17, The Royal Society of Chemistry 2007.
Wang et al., "Effect of Support Nature on WO3/SiO2 Structure and Butene-1 Metathesis", Applied Catalysis A: General, 2003, 25-37, 250, Elsevier B.V.
Zhao et al., "Effect of Tungsten Oxide Loading on Metathesis Activity of Ethene and 2-Butene Over WO3/SiO2 Catalysts" Transition Met Chem, 2009, 621-27, 34, Springer.

* cited by examiner

SYSTEMS AND METHODS FOR PRODUCING PROPYLENE

CROSS-REFERENCE TO RELATED APPLICATIONS

This application claims the benefit of U.S. Provisional Application Ser. No. 62/188,068 filed Jul. 2, 2015, the entire contents of which are incorporated by reference.

BACKGROUND

Field

The present disclosure generally relates to processes and systems for producing propylene, and more specifically, to processes and systems for producing propylene from process streams comprising butene.

Technical Background

In recent years, there has been a dramatic increase in the demand for propylene to feed the growing markets for polypropylene, propylene oxide, and acrylic acid. Currently, most of the propylene produced worldwide is a byproduct from steam cracking units which primarily produce ethylene, or a by-product from FCC units which primarily produce gasoline. These processes cannot respond adequately to a rapid increase in propylene demand.

Other propylene production processes contribute to the total propylene production. Among these processes are propane dehydrogenation (PDH), metathesis reactions requiring both ethylene and butene, high severity FCC, olefins cracking, and methanol to olefins (MTO). However, propylene demand has increased and propylene supply has not kept pace with this increase in demand.

Regarding the production of propylene by metathesis requiring ethylene and butene, generally, a stoichiometric ratio of about 1 butene to 1 ethylene is desirable for high product yield. However, in some cases, ethylene is not available, or is not available in great enough quantities compared to butene supply. Therefore, such processes requiring butene and ethylene may not be feasible due to lack of ethylene supply available for reaction. Accordingly, ongoing needs exist for a process for efficiently converting butene to propylene, and specifically for efficiently converting butene to propylene without the need for ethylene.

BRIEF SUMMARY

In accordance with one embodiment of the present disclosure, propylene may be produced by a process comprising at least partially metathesizing a first portion of a first stream to form a first metathesis-reaction product, least partially cracking the first metathesis-reaction product to form a cracking-reaction product, at least partially separating ethylene from at least the cracking reaction product to form a first recycle stream, combining the first recycle stream with a second portion of the first stream to a form a mixed stream, and at least partially metathesizing the mixed stream to from a second metathesis-reaction product. According to embodiments, the first stream may comprise butene, the cracking reaction product may comprise propylene and ethylene, the first recycle stream may comprise ethylene, and the second metathesis-reaction product may comprise propylene.

In accordance with another embodiment of the present disclosure, propylene may be produced by a process comprising introducing a first portion of a first stream comprising butene to a first reactor, at least partially metathesizing the first portion of the first stream with the first metathesis catalyst to form a first metathesis-reaction product, at least partially cracking the first metathesis-reaction product with a cracking catalyst to produce a cracking-reaction product, passing the cracking-reaction product out of the first reactor in a cracking-reaction product stream, combining a first recycle stream with a second portion of the first stream to a form a mixed stream and introducing the mixed stream to a second reactor, at least partially metathesizing the mixed stream with a second metathesis catalyst in the second reactor to produce a second metathesis-reaction product and passing the second metathesis-reaction product out of the second reactor in a second metathesis-reaction product stream. The process may further comprise at least partially separating ethylene from the cracking-reaction product stream, the second metathesis-reaction product stream, or a stream comprising a mixture of both, to form the first recycle stream. Additionally, the process may comprise at least partially separating propylene from the cracking-reaction product stream, second metathesis-reaction product stream, or a stream comprising a mixture of both, to form a product stream comprising propylene. According to embodiments, the first reactor may comprise a first metathesis catalyst and a cracking catalyst, the cracking-reaction product may comprise propylene and ethylene, the first metathesis catalyst may be positioned generally upstream of the cracking catalyst, the second reactor may comprise a second metathesis catalyst, and the second metathesis-reaction product may comprise propylene.

In accordance with yet another embodiment of the present disclosure, propylene may be produced by a process comprising introducing a first portion of a first stream comprising butene to a first reactor, at least partially metathesizing the first portion of the first stream with a first metathesis catalyst to form a first metathesis-reaction product, introducing the first metathesis-reaction product to a second reactor, at least partially cracking the first metathesis-reaction product with a cracking catalyst to produce a cracking-reaction product comprising propylene and ethylene, passing the cracking-reaction product out of the second reactor in a cracking-reaction product stream, combining an ethylene recycle stream with a second portion of the first stream comprising butene to a form a mixed stream and introducing the mixed stream to a third reactor, at least partially metathesizing the mixed stream with the second metathesis catalyst in the third reactor to produce a second metathesis-reaction product comprising propylene and passing the second metathesis-reaction product out of the third reactor in a second metathesis-reaction product stream. The process may further comprise at least partially separating ethylene from the cracking-reaction product stream, the second metathesis-reaction product stream, or a stream comprising a mixture of both, to form the ethylene recycle stream. Additionally, the process may further comprise at least partially separating propylene from the cracking-reaction product stream, the second metathesis-reaction product stream, or a stream comprising a mixture of both, to form a product stream comprising propylene. According to embodiments, the first reactor may comprise a first metathesis catalyst and a cracking catalyst, and the third reactor may comprise a second metathesis catalyst.

In accordance with yet another embodiment of the present disclosure, systems may be operable to perform the processes for producing propylene described in this disclosure.

Additional features and advantages of the technology described in this disclosure will be set forth in the detailed description which follows, and in part will be readily apparent to those skilled in the art from the description or recognized by practicing the technology as described in this disclosure, including the detailed description which follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
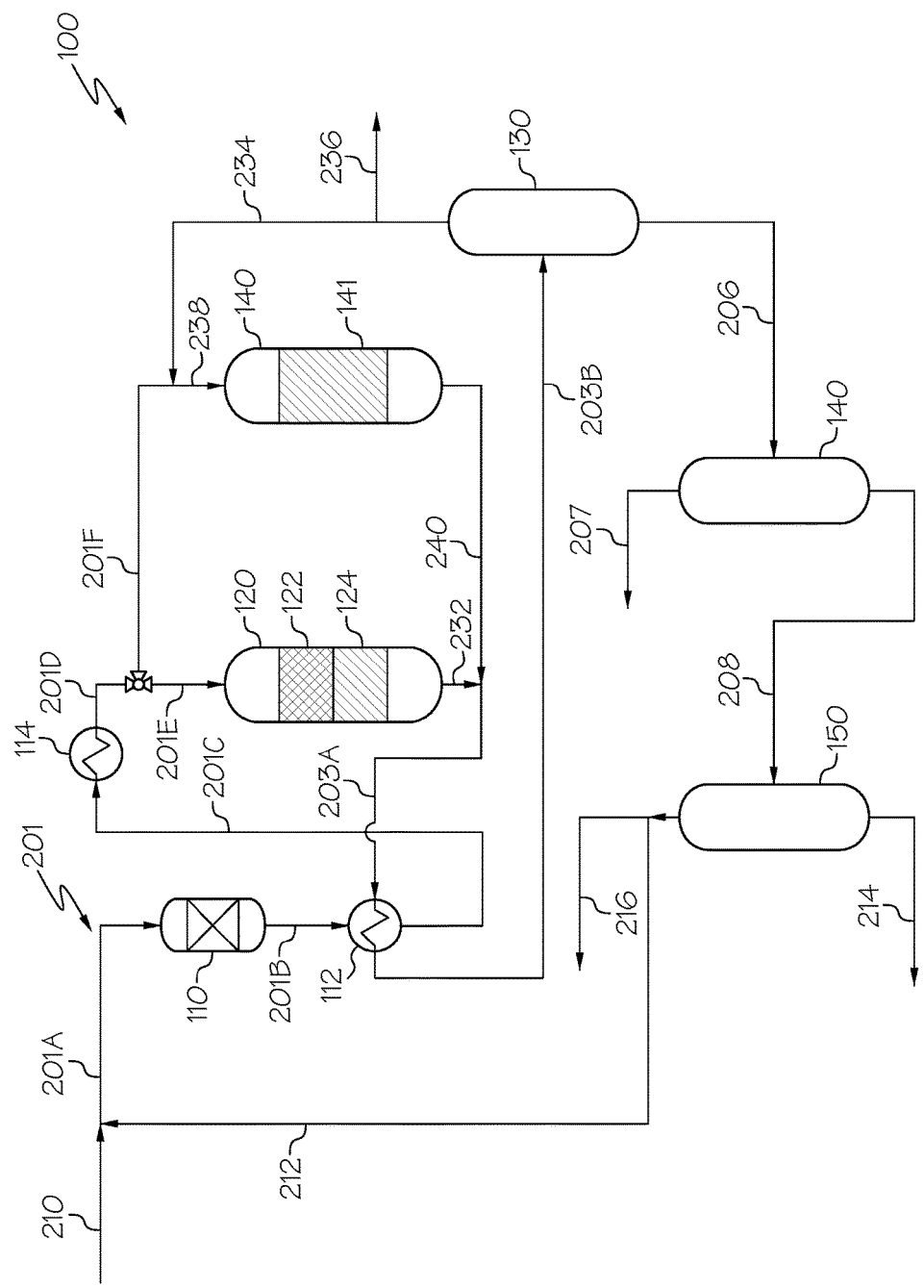
FIG. 1 is a generalized diagram of a first butene conversion system, according to one or more embodiments described in this disclosure.
Figure 2:
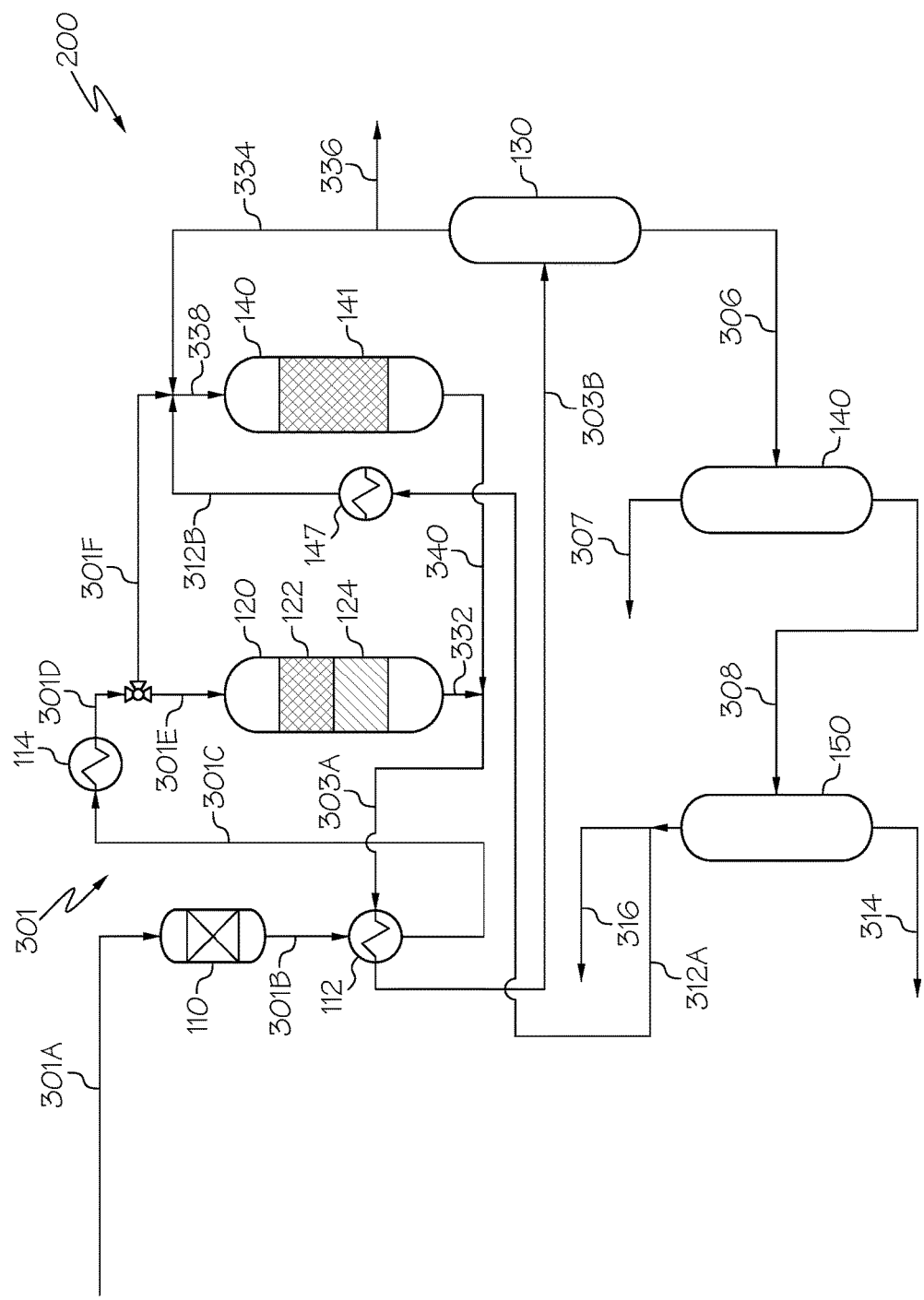
FIG. 2 is a generalized diagram of a second butene conversion system, according to one or more embodiments described in this disclosure.

For the purpose of the simplified schematic illustrations and descriptions of FIGS. 1 and 2, the numerous valves, temperature sensors, electronic controllers and the like that may be employed and well known to those of ordinary skill in the art of certain refinery operations are not included. Further, accompanying components that are in conventional refinery operations including catalytic conversion processes such as, for example, air supplies, catalyst hoppers, and flue gas handling are not depicted. However, operational components, such as those described previously, may be added to the embodiments described in this disclosure.

It should further be noted that arrows in the drawings refer to transfer lines which may serve to transfer steams between two or more system components. Additionally, arrows that connect to system components define inlets or outlets, or both, in each given system component. The arrow direction corresponds generally with the major direction of movement of the materials of the stream contained within the physical transfer line signified by the arrow. Furthermore, arrows which do not connect two or more system components signify a product stream which exits the depicted system or a system inlet stream which enters the depicted system. Product streams may be further processed in accompanying chemical processing systems or may be commercialized as end products. System inlet streams may be streams transferred from accompanying chemical processing systems or may be non-processed feedstock streams.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Generally, described in this disclosure are various embodiments of systems and methods for converting butene into propylene. Generally, the conversion system includes components which are operable to carry out a method where a stream comprising butene in split into two portions, where the first portion undergoes a metathesis reaction and a cracking reaction to form propylene and ethylene. The second portion of the stream comprising butene is combined with a stream comprising ethylene. The combined stream comprising butene and ethylene is metathesized. Thus, with reference to the stream comprising butene, a metathesis/cracking reaction and a metathesis reaction are performed in a parallel system arrangement. The products of these two reactor units (that is, the metathesis/cracking product stream and the cracking product stream) may optionally be combined and components of the two streams may be recovered by one or more separation processes. For example, a propylene stream may be recovered by at least partially separating propylene from at least one of the metathesis/cracking product stream, the cracking product stream, or the mixture of the two streams. Additionally, the stream comprising ethylene, which is combined with the second portion of the stream comprising butene can be a system recycle stream derived from a separation of ethylene from other components of one or more of the product streams.

Furthermore, following the reactions of the first portion and second portion of the stream comprising butene, the reaction product streams may be separated into multiple process streams, where some streams may optionally be recycled back into the system. Thus, the systems may operate with a single system inlet stream comprising at least about 50 wt. % butene, such as raffinate streams created from a naphtha cracking process. The systems generally do not require a system inlet comprising ethylene, as the ethylene consumed in the reaction of the system is self produced from the metathesis reaction of the first portion of the butene stream.

As used in this disclosure, "transfer lines" may include pipes, conduits, channels, or other suitable physical transfer lines that connect by fluidic communication one or more system components to one or more other system components. As used in this disclosure, a "system component" refers to any apparatus included in the system, such as, but not limited to, separation units, reactors, heat transfer devices such as heaters and heat exchangers, filters, impurities removal devices, combinations of each, and the like. A transfer line may generally carry a process stream between two or more system components. Generally, a transfer line may comprise multiple segments, where a "segment" of a transfer line includes one or more portions of a transfer line, such that a transfer line may comprise multiple transfer line segments. Generally, the chemical composition of a process stream in a particular transfer line is similar or identical throughout the entire length of the transfer line. However, it should be appreciated that the temperature, pressure, or other physical properties of a process stream may change through a transfer line, particularly in different transfer line segments. Also, relatively minor compositional changes in a process stream may take place over the length of a transfer line, such as the removal of an impurity. Also, sometimes the systems described in this disclosure are referred to as "butene conversion systems," which refers to any system which at least partially converts butene into one or more other chemical species. For example, in some embodiments, butene is at least partially converted into propylene. As described in this disclosure, the butene conversion systems are suitable to process streams comprising butene, including streams that are substantially free of other alkenes (for example, ethylene, propene), into a product process stream comprising a significant amount of propylene. As used in this disclosure, a stream or composition does "not substantially comprise" or "is substantially free" of a component when that component is present in an amount of less than 0.1 wt. %.

As used in this disclosure, a "separation unit" refers to any separation device that at least partially separates one or more chemicals that are mixed in a process stream from one another. For example, a separation unit may selectively separate differing chemical species from one another, forming one or more chemical fractions. Examples of separation units include, without limitation, distillation columns, flash drums, knock-out drums, knock-out pots, centrifuges, filtration devices, traps, scrubbers, expansion devices, membranes, solvent extraction devices, and the like. It should be understood that separation processes described in this disclosure may not completely separate all of one chemical consistent from all of another chemical constituent. It should be understood that the separation processes described in this disclosure "at least partially" separate different chemical components from one another, and that even if not explicitly stated, it should be understood that separation may include only partial separation. As used in this disclosure, one or more chemical constituents may be "separated" from a process stream to form a new process stream. Generally, a process stream may enter a separation unit and be divided, or separated, into two or more process streams of desired composition. Further, in some separation processes, a "light fraction" and a "heavy fraction" may exit the separation unit, where, in general, the light fraction stream has a lesser boiling point than the heavy fraction stream.

As used in this disclosure, a "reactor" refers to a vessel in which one or more chemical reactions may occur between one or more reactants optionally in the presence of one or more catalysts. For example, a reactor may include a tank or tubular reactor configured to operate as a batch reactor, a continuous stirred-tank reactor (CSTR), or a plug flow reactor. Example reactors include packed bed reactors such as fixed bed reactors, and fluidized bed reactors. A reactor may comprise one or more catalyst sections, such as catalyst beds, where a "section" is the area of the reactor which houses a particular catalyst or group of multiple catalysts. In another embodiment, separation and reactions may take place in a reactive separation unit.

As used in this disclosure, a "catalyst" refers to any substance which increases the rate of a specific chemical reaction. Catalysts described in this disclosure may be utilized to promote various reactions, such as, but not limited to, metathesis or cracking reactions, or both. As used in this disclosure, a "metathesis catalyst" increases the rate of a metathesis reaction, and a "cracking catalyst" increases the rate of a cracking reaction. As used in this disclosure "metathesis" generally refers to a chemical reaction where fragments of alkenes (olefins) are redistributed by the scission and regeneration of alkene bonds. Also, as used in this disclosure, "cracking" generally refers to a chemical reaction where a molecule having carbon to carbon bonds is broken into more than one molecule by the breaking of one or more of the carbon to carbon bonds. The resulting cracked molecules may have combined the same number of carbon atoms as the original molecule prior to cracking.

Examples of metathesis catalysts and cracking catalysts are disclosed in co-pending Saudi Aramco U.S. Provisional Patent Application No. 62/181,178 entitled "Dual Catalyst System for Propylene Production" and co-pending Saudi Aramco U.S. Provisional Patent Application No. 62/181,129 entitled "Propylene Production Using a Mesoporous Silica Foam Metathesis Catalyst", each of which are incorporated by reference in their entirety in this disclosure. As noted it that disclosure, suitable metathesis catalysts may include mesoporous silica catalysts impregnated with metal oxide. Suitable cracking catalysts may include mordenite framework inverted (MFI) structured silica catalysts. The mesoporous silica catalysts may include a pore size distribution of from about 2.5 nm to about 40 nm and a total pore volume of at least about 0.600 $cm^3/g$ (cubic centimeters per gram). However, it should be understood that the systems described in this disclosure may include any suitable metathesis catalysts and cracking catalysts, such as commercially available catalysts or catalysts which are the subject of future discovery.

The suitable reaction conditions for metathesis and cracking reactions described in this disclosure may vary by the catalyst compositions employed. However, in some embodiments, the metathesis or cracking reactions, or both, may take place at temperatures from about 500° C. (degrees Celsius) to about 600° C. in atmospheric pressure.

As described in this disclosure, "butene" may include at least 1-butene, isobutene, cis-2-butene, trans-2-butene 2-methyl-2-butene, 3-methyl-1-butene, 2-methyl-1-butene, and cyclobutene. Butene is sometimes referred to as butylene, and the terms "butene" and "butylene" may be used interchangeably in this disclosure. As described in this disclosure, "pentene" may include at least 1-pentene, cis-2-pentene, trans-2-pentene, 4-methyl-trans-2-pentene, cyclopentene, and 2-methyl-2-pentene. As described in this disclosure, "hexene" may include at least trans-2-hexene, trans-3-hexene, cis-3-hexene, and cyclohexene. In this disclosure, certain chemicals may be referred to in shorthand notation, where C2 stands for ethane, C3 stands for propane, C4 stands for ethane, C5 stands for pentane, C6 stands for hexane, C3=stands for propylene (or propene), C4=stands for butene (or butylene), C5=stands for pentene, and C6=stands for hexene.

It should be understood that when two or more process stream are "mixed" or "combined" when two or more lines intersect in the schematic flow diagrams of FIGS. 1 and 2. Mixing or combining may also include mixing by directly introducing both streams into a like reactor, separation device, or other system component.

It should be understood that while the embodiments of FIGS. 1 and 2 may have varying mechanical apparatus or process stream compositions, or both, these embodiments generally share many of the same system components and transfer lines. As such, processes which occur in like system components in the various embodiments of FIGS. 1 and 2 may be similar or identical with one another. For example, the system components of FIGS. 1 and 2 marked with the same reference number may perform similar or identical operations in the various embodiments. Some process streams in the embodiments of FIGS. 1 and 2 may comprise similar or identical compositions, while others may not. For clarity, the transfer lines of the embodiments of FIGS. 1 and 2 have each been given different reference numbers so that the composition of their contained stream may be easily identified. However, while some transfer lines may be in like areas and have like functions in the various embodiments of FIGS. 1 and 2, they may have substantially different compositions (such as in cases where recycle streams are present or where recycle streams reenter at differing system locations). Some process streams contained in like areas of FIGS. 1 and 2 may be similar or even identical in like processing conditions (for example, like inlet stream composition). For example, the streams of transfer lines/segments such as, but not limited to: 210 and 301A may be similar or substantially identical in composition; 236 and 336 may be similar or substantially identical in composition; 234 and 334 may be similar or substantially identical in composition; 207 and 307 may be similar or substantially identical in composition; 216 and 316 may be similar or substantially identical in composition; and 206 and 406 may be similar or substantially identical in composition. The Examples, as provided in this disclosure, further clarify the differences in stream compositions between the various embodiments.

Referring now to the process-flow diagram of FIG. 1, in one embodiment, a butene conversion system 100 may include a metathesis/cracking reactor 120 which comprises a metathesis catalyst section 122 and a cracking catalyst section 124. Generally, a system inlet stream comprising butene enters the butene conversion system 100 through transfer line 210. The system inlet stream generally comprises at least butene, and may optionally comprise other chemical species such as butane. For example, the system inlet stream may comprise at least about 20 wt. %, 30 wt. %, 40 wt. %, 50 wt. %, 55 wt. %, 60 wt. %, 65 wt. %, or even at least about 70 wt. % butene. The system inlet stream of transfer line 210 may comprise at least about 15 wt. %, 20 wt. %, 25 wt. %, 30 wt. %, or even at least about 35 wt. % butane, and may comprise from 0 wt. % to about 10 wt. %, 8 wt. %, 2 wt. %, or 4 wt. % ethylene, or may not substantially comprise ethylene. The system inlet stream in transfer line 210 is combined with a recycle stream in transfer line 212 to form a mixed stream present in transfer line 201. The mixed stream is passed through transfer line segments 201A, 201B, 201C, and 201D, and is split into two mixed stream portions located in transfer line segments 201E and 201F. The mixed stream in transfer line segment 201E is injected into the metathesis/cracking reactor 120.

In embodiments, the recycle stream of transfer line 212 may comprise butene and butane. For example, the recycle stream of transfer line 212 may comprise at least about 5 wt. %, 10 wt. %, 15 wt. %, or even at least about 20 wt. % butene, and may comprise at least about 50 wt. %, 60 wt. %, 70 wt. %, or even greater than about 80 wt. % butane. The recycle stream of transfer line 212 may comprise at least about 80 wt. %, 90 wt. % or even at least about 95 wt. % of butane and butene. The mixed stream of transfer line 201 may comprise butane and butene. For example, the mixed stream of transfer line 201 may comprise at least about 5 wt. %, 10 wt. %, 15 wt. %, 20 wt %, 25 wt. %, 30 wt. %, or even at least about 35 wt. % butene, and may comprise at least about 40 wt. %, 50 wt. %, 60 wt. %, 70 wt. %, or even greater than about 80 wt. % butane. The mixed stream of transfer line 201 may comprise at least about 80 wt. %, 90 wt. % or even at least about 95 wt. % of the combination of butane and butene.

In one embodiment, the mixed stream may be split in a first mixed stream portion in transfer line segment 201E and a second mixed stream portion in transfer line segment 201F where the ratio of the mass flowrate of the first mixed stream portion to the flowrate of the second mixed stream portion is between about 2:1 and 3:1, 1.5:1 and 4:1, or 1:1 to 6:1.

The mixed stream may be processed by one or more system components prior to being split into the streams of segments 201E and 201F. In some embodiments, the transfer line 201 may comprise several segments (depicted as 201A, 201B, 201C, and 201D) which may be separated by system components such as an impurities removal device 110, heat transfer device 112, and heat transfer device 114. The impurities removal device 110 may remove oxygenates present in the mixed stream. In one embodiment, the impurities removal device comprises a catalytic bed. Heat transfer device 112 may be a heat exchanger that serves to elevate the temperature of the mixed stream by exchanging energy with the stream present in transfer line 203A. Heat transfer device 114 may be a heater that serves to further heat the mixed stream. It should be understood that the impurities removal device 110, heat transfer device 112, and heat transfer device 114 are optional components in the butene conversion system 100. It should be understood that all streams located in the various segments of transfer line 201 (that is, 201A, 201B, 201C, 201D, 201E, and 201F) are considered portions of the mixed stream, even though the chemical composition, temperature, or other properties of the system inlet stream may be different in the various segments 201A, 201B, 201C, 201D, 201E, and 201F.

Still referring to FIG. 1, the metathesis catalyst section 122 is positioned generally upstream of the cracking catalyst section 124, that is, the cracking catalyst section 124 is positioned generally downstream of the metathesis catalyst section 122. The portion of the mixed stream of segment 201E enters the metathesis/cracking reactor 120 and undergoes a metathesis reaction in the metathesis catalyst section 122 to form a metathesis-reaction product. Following the metathesis reaction, the metathesis-reaction product is cracked in a cracking reaction in the cracking catalyst section 124. The cracking reaction forms a cracking-reaction product. Generally, the reactants that undergo cracking or metathesis, or both, intimately intermingle with the respective catalysts during reaction.

As used in this disclosure, a "metathesis-reaction product" refers to the entire product mixture resulting from the metathesis reaction, including any portion of the metathesis-product stream which does not undergo metathesis. Additionally, as used in this disclosure "cracking-reaction product" refers to the entire product mixture resulting from the cracking reaction, including any portion of the cracking-product mixture which does not undergo cracking.

The cracking-reaction product is passed out of the metathesis/cracking reactor 120 in a cracking-reaction product stream via transfer line 232. The cracking-reaction product of transfer line 232 may comprise, consist, or consist essentially of a mixture of alkanes and alkenes, including, but not limited to, one or more of ethylene, propylene, butene, pentene, hexene, heptene, ethane, propane, butane, pentane, hexane, and heptane. The cracking-reaction product may comprise at least about 2 wt. %, 4 wt. %, 6 wt. %, 8 wt. %, 10 wt. %, 12 wt. %, 14 wt. %, 16 wt. %, 18 wt. %, 20 wt. %, 22 wt. %, 24 wt. %, 26 wt. %, 28 wt. %, or even at least about 30 wt. % propylene.

The portion of the mixed stream that is present in segment 201F is combined with an ethylene recycle stream present in transfer line 234. The ethylene recycle stream may be generated from the separation process of separation unit 130, which will be described in this disclosure. Generally, the ethylene recycle stream of transfer line 234 comprises at least about 50 wt. %, 60 wt. %, 70 wt. %, 80 wt. %, 90 wt. %, 95 wt. %, 96 wt. %, 97 wt. %, 98 wt. %, or even at least about 99 wt. % ethylene. The combination of the mixed stream of segment 201F and the ethylene recycle stream of transfer line 234 forms a butene/ethylene mixed stream present in transfer line 238.

Still referring to FIG. 1, the metathesis reactor 140 comprises a metathesis catalyst section 141, such as a metathesis catalyst bed. The metathesis reactor 140 and the metathesis/cracking reactor 120 are arranged in parallel relative to the mixed stream of transfer line 201. The butene/ethylene stream from transfer line 238 enters the metathesis reactor 140 and undergoes a metathesis reaction in the metathesis catalyst section 141 to form a metathesis-reaction product. The metathesis-reaction product may be passed out of the metathesis reactor in a metathesis-reaction product stream via transfer line 240. The metathesis-reaction product of transfer line 240 may comprise, consist, or consist essentially of a mixture of alkanes and alkenes, including, but not limited to, one or more of ethylene, propylene, butene, pentene, hexene, heptene, ethane, propane, butane, pentane, hexane, and heptane. The metathesis-reaction product of transfer line 240 may comprise at least about 2 wt. %, 4 wt. %, 6 wt. %, 8 wt. %, 10 wt. %, 12 wt. %, 14 wt. %, 16 wt. %, 18 wt. %, 20 wt. %, 22 wt. %, 24 wt. %, 26 wt. %, 28 wt. %, or even at least about 30 wt. % propylene.

The metathesis-reaction product stream of transfer line 240 may be combined with the cracking-reaction product stream of transfer line 232 to form a mixed product stream of transfer line 203 (including segments 203A and 203B). In one embodiment, as shown in FIG. 1, the mixed product stream of transfer line 203 may exchange heat with the mixed stream of segment 201B via heat transfer device 112.

The mixed-reaction product stream of transfer line segment 203B may be separated into one or more streams having desired compositions. Generally, a product stream comprising propylene, such as shown in transfer line 207 in FIG. 1, may be formed by separating propylene in the mixed-reaction product stream. Additionally, the ethylene recycle stream of transfer line 234 may be separated from the mixed-reaction product stream of transfer line segment 203B. The propylene product stream may comprise at least about 50 wt. %, 60 wt. %, 70 wt. %, 80 wt. %, 90 wt. %, 95 wt. %, 96 wt. %, 97 wt. %, 98 wt. %, or even at least about 99 wt. % propylene. It should be understood that a wide variety of separation processes may be utilized to produce the product stream comprising propylene.

In one embodiment, as shown in FIG. 1, the mixed-reaction product stream of transfer line segment 203 may be introduced to one or more separation units, such as separation unit 130. The mixed reaction product may enter separation unit 130 where light constituents, such and ethane and ethylene, may be removed. Light constituents such as ethylene may be purged from the butene conversion system 100 via transfer line 236 or may be utilized as the ethylene recycle stream via transfer line 234. The streams contained in transfer line 234 and transfer line 236 may comprise, consist, or consist essentially of ethylene. For example, the stream of transfer line 204 or transfer line 205, or both, may comprise at least about 50 wt. %, 60 wt. %, 70 wt. %, 80 wt. %, 90 wt. %, 95 wt. %, 96 wt. %, 97 wt. %, 98 wt. %, or even at least about 99 wt. % ethylene. The heavy fraction from separation unit 130 may be passed out of separation unit 130 via transfer line 206. The stream of line 206 may comprise a mixture of alkanes and alkenes, including, but not limited to, one or more of propylene, butene, pentene, hexene, heptene, ethane, propane, butane, pentane, hexane, and heptane. The stream of transfer line 206 may enter separation unit 140 where propylene is separated from other constituents. The light fraction (that is, propylene) may exit the separation unit 140 via transfer line 207 as a propylene product stream. The propylene product stream contained in transfer line 207 may comprise, consists, or consist essentially of propylene. For example, the stream of transfer line 204 or transfer line 205, or both, may comprise at least about 50 wt. %, 60 wt. %, 70 wt. %, 80 wt. %, 90 wt. %, 95 wt. %, 96 wt. %, 97 wt. %, 98 wt. %, or even at least about 99 wt. % propylene. The heavy fraction from separation unit 140 may be passed out of separation unit 140 via transfer line 208. The stream of line 208 may comprise a mixture of alkanes and alkenes, including, but not limited to, one or more of butene, pentene, hexene, heptene, ethane, propane, butane, pentane, hexane, and heptane.

The stream of transfer line 208 may be injected into separation unit 150 where one or more fractions may be separated from one another. In one embodiment, a bottoms fraction may exit separation unit 150 in a stream contained in transfer line 214. The stream of transfer line 214 may comprise one or more of butene, pentene, pentane, hexene, heptene, and butane. The top fraction, which comprises primarily butene and butane, may exit separation unit 150 in the recycle stream contained in transfer line 212. A portion of the recycle stream contained in transfer line 212 may be purged from the system 100 via transfer line 216. The remaining portion may be recycled into the system 100 by combining the recycle stream of transfer line 212 with the system inlet stream of transfer line 210. In embodiments, the recycle stream of transfer line 212 may comprise at least about 5 wt. %, 10 wt. %, 15 wt. %, 20 wt. %, 25 wt. %, 30 wt. %, or even at least about 35 wt. % butene, and may comprise at least about 40 wt. %, 50 wt. %, 60 wt. %, 70 wt. %, or even greater than about 80 wt. % butane. The recycle stream of transfer line 512 may comprise at least about 80 wt. %, 90 wt. %, or even at least about 95 wt. % of butane and butene.

FIG. 2 depicts an embodiment which is similar to that of FIG. 1, but the recycle stream comprising butene (shown in transfer line 312) mixes into a different portion of the butene conversion system 200. As shown in FIG. 2, the butene conversion system 200 comprises a recycle stream in transfer line 312 (including segments 312A and 312B) which is combined with the streams of transfer line segment 301F and transfer line 334. In embodiments, the recycle stream of transfer line 312 may comprise at least about 5 wt. %, 10 wt. %, 15 wt. %, 20 wt. %, 25 wt. %, 30 wt. %, or even at least about 35 wt. % butene, and may comprise at least about 40 wt. %, 50 wt. %, 60 wt. %, 70 wt. %, or even greater than about 80 wt. % butane. The recycle stream of transfer line 512 may comprise at least about 80 wt. %, 90 wt. %, or even at least about 95 wt. % of butane and butene.

In the embodiment of FIG. 2, since the recycle stream of transfer line 312 does not combine with the inlet stream 301, the process stream entering the metathesis/cracking reactor 120 is the inlet stream of transfer line 301. The cracking-reaction product of transfer line 332 may comprise, consist, or consist essentially of a mixture of alkanes and alkenes, including, but not limited to, one or more of ethylene, propylene, butene, pentene, hexene, heptene, ethane, propane, butane, pentane, hexane, and heptane. The cracking-reaction product may comprise at least about 2 wt. %, 4 wt. %, 6 wt. %, 8 wt. %, 10 wt. %, 12 wt. %, 14 wt. %, 16 wt. %, 18 wt. %, 20 wt. %, 22 wt. %, 24 wt. %, 26 wt. %, 28 wt. %, or even at least about 30 wt. % propylene.

It should be appreciated the butene conversion systems described in this disclosure do not require a recycle stream comprising butene (as is present in the transfer lines of 212 in the embodiment of FIG. 1 and transfer line 312 in the embodiment of FIG. 2). For example, in embodiments, the process stream of transfer line 208 may be expelled from the butene conversion system. In other embodiments, the recycle streams of FIGS. 1 and 2 may be employed in the same system.

Referring to the embodiments of FIGS. 1 and 2, it should be appreciated that the flowrate of the process stream of transfer line 236 and 336 may be controlled based on the desire to utilize the ethylene of transfer lines 236 and 336 in outside processes or sale for commercial gain. For example, if ethylene is commercially marketable relative to propylene, its flowrate may be increased. Additionally, it should be appreciated that other system streams may be changed in reaction to a change in the flowrate of transfer lines 236 and 336. For example, if the flowrate of transfer line 236 or 336 is increased, less ethylene will be available for the metathesis reaction in reactor 140. Therefore, in some embodiments, the amount of propylene supplied to the metathesis reactor 140 should be reduced by reducing the flowrate of at least transfer line segment 201F, 301F, or 312A, or each.

In another embodiment, the butene conversion systems described in this disclosure may comprise multiple reactors in series in place of a metathesis/cracking reactor 120. In some embodiments, it may be advantageous to utilize reactors in series when the metathesis reaction and cracking reaction are performed at different conditions (such as temperature or pressure). In such embodiments, the system may comprise a metathesis reactor which comprises a metathesis catalyst section, such as a metathesis catalyst bed, and a cracking reactor which comprises a cracking catalyst section, such as a cracking catalyst bed. In such an embodiment, the metathesis reactor and the cracking reactor are arranged in series where the metathesis reactor is positioned generally upstream of the cracking reactor, that is, the cracking reactor is positioned generally downstream of the metathesis reactor. With reference to FIG. 1, an inlet stream from segment 201E enters a metathesis reactor and undergoes a metathesis reaction to form a metathesis-reaction product. The metathesis-reaction product may then be passed out of the metathesis reactor in a metathesis-reaction product stream. The metathesis-reaction product stream then enters a cracking reactor and is cracked in a cracking reaction. The cracking reaction forms a cracking-reaction product. The cracking-reaction product is passed out of the cracking reactor in a cracking-reaction product stream, similar to the stream 232 of FIG. 1. Examples of separate metathesis and cracking reactors arranged in series are available in co-pending Saudi Aramco U.S. Provisional Patent Application No. 62/181,052 entitled "Systems and Methods for Producing Propylene", which is incorporated by reference in its entirety in this disclosure. Such dual reactor systems could be integrated into the systems of FIGS. 1 and 2 by replacing reactor 120 with two reactors in series.

Generally, a stream containing butane and butene, suitable as the inlet stream in the embodiments described in this disclosure, may be produced from refining operations. This stream containing butane and butene may be separated into fractions to form a first raffinate, second raffinate, and third raffinate. In one embodiment, the system inlet stream may be a raffinate stream from an olefin refining system, such as a conventional refinery. The stream produced from the refining operation may generally comprise C4 alkanes and alkenes, including butanes, butenes, and butadienes. A "first raffinate" may be produced by separating 1,3-butadiene from the other C4 constituents in the stream. The first raffinate may comprise isobutylene, cis-2-butene, and trans-2-butene. For example, the first raffinate may comprise, or consist essentially of, from about 40 wt. % to about 50 wt. %, from about 35 wt. % to about 55 wt. %, or from about 30 wt. % to about 60 wt. % of isobutene and from about 30 wt. % to about 35 wt. %, from about 25 wt. % to about 40 wt. %, or from about 20 wt. % to about 45 wt. % of the sum of cis-2-butene and trans-2-butene. A "second raffinate" may be produced by separating isobutylene from the other C4 constituents of the first raffinate. For example, the second raffinate may comprise, or consist essentially of, from about 50 wt. % to about 60 wt. %, from about 45 wt. % to about 65 wt. %, or from about 40 wt. % to about 70 wt. % of the sum of cis-2-butene and trans-2-butene, from about 10 wt. % to about 15 wt. %, from about 5 wt. % to about 20 wt. %, or from about 0 wt. % to about 25 wt. % of 1-butene, and from about 15 wt. % to about 25 wt. %, from about 10 wt. % to about 30 wt. %, or from about 5 wt. % to about 35 wt. % of butane. The inlet stream of the systems described herein may be substantially free of isobutene, and may consist essentially of 2-butenes and n-butanes.

EXAMPLES

The various embodiments of methods and systems for the cracking of a light fuel fraction and a heavy fuel fraction by fluidized catalytic cracking will be further clarified by the following examples. The examples are illustrative in nature, and should not be understood to limit the subject matter of the present disclosure.

Example 1

Figure 3:
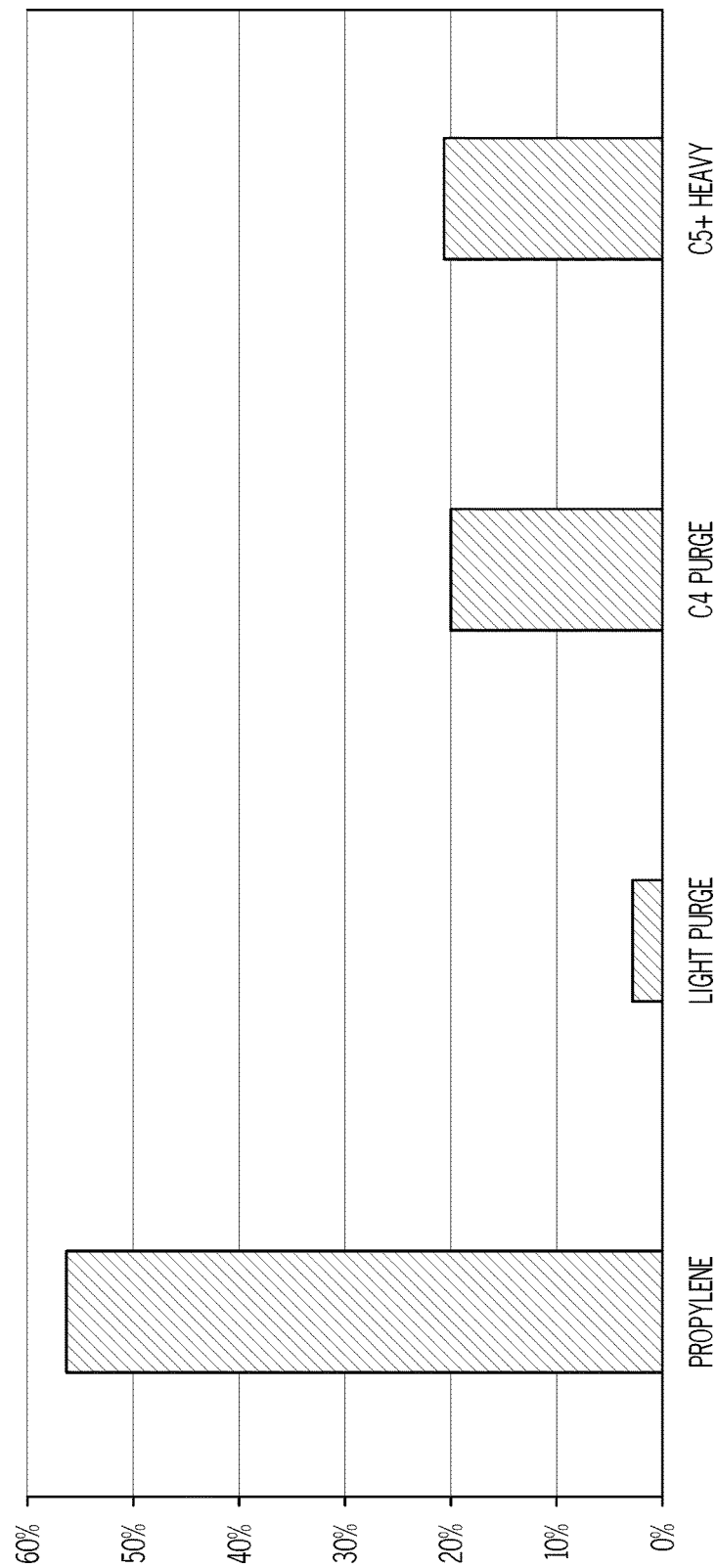
FIG. 3 depicts a bar graph displaying the product distribution in wt. % (weight percent) of the system of FIG. 1, according to one or more embodiments described in this disclosure.

The systems of FIG. 1 was computer modeled using Aspen Plus® (commercially available from AspenTech). The subsequent tables (Tables 1-4) depict the stream compositions and flowrates, as well as thermal properties for selected streams. The reaction rates supplied for the simulation were representative of experimental reaction rates for the metathesis catalyst W-SBA-15 and the cracking catalyst MFI-2000, as described in Examples 1, 3, and 6 of co-pending Saudi Aramco U.S. Provisional Patent Application No. 62/181,178 entitled "Dual Catalyst System for Propylene Production". A system inlet stream of 35 wt. % cis-2-butene, 35 wt. % trans-2-butene, and 30 wt. % n-butane was used for the model. The stream numbers corresponds with the stream or stream segment shown in FIG. 1. Simulations were run for 100% efficiency and 80% efficiency. Data for the simulations is provided on a weight basis and a mole basis for each simulation. Specifically, Table 1 depicts data for a simulation of the system of FIG. 1 with 100% efficiency and shows components on a mass basis. Table 2 depicts data for a simulation of the system of FIG. 1 with 100% efficiency and shows components on a mole basis. Table 3 depicts data for a simulation of the system of FIG. 1 with 80% efficiency and shows components on a mass basis. Table 4 depicts data for a simulation of the system of FIG. 1 with 80% efficiency and shows components on a mole basis. Additionally, FIG. 3 depicts a bar graph displaying the product distribution of the system of FIG. 1 as shown in Table 1 where, on the bar graph, "Propylene" corresponds with the stream of transfer line 207, "Light Purge" corresponds with the stream of transfer line 236, "C4 Purge" corresponds with the stream of transfer line 216, and "C5+ Heavy" corresponds with the stream of transfer line 214.

TABLE 1

| FIG. 1 with 100% efficiency in wt. % | | | | | | | | |
|---|---|---|---|---|---|---|---|---|
| Stream Number | 210 | 201A/B/C/D | 201E | 232 | 201F | 238 | 240 | 203A/B |
| Mole Flow, kmol/hr | 100.0 | 277.5 | 194.3 | 214.7 | 83.3 | 134.6 | 134.6 | 349.3 |
| Mass Flow, kg/hr | 5670 | 15918 | 11143 | 11143 | 4775 | 6221 | 6221 | 17364 |
| Volumn Flow m$^3$/hr | 6750 | 10562 | 7393 | 10556 | 3169 | 4199 | 9091 | 28.4 |
| Enthalpy, MW | 0.6 | −3.6 | −2.5 | −1.3 | −1.1 | −0.7 | 0.8 | −5.5 |
| MW, g/mol | 56.7 | 57.4 | 57.4 | 51.9 | 57.4 | 46.2 | 46.2 | 49.7 |
| Density, kg/m$^3$ | 0.84 | 1.51 | 1.51 | 1.06 | 1.51 | 1.48 | 0.68 | 610.5 |
| COMPONENTS, wt % | | | | | | | | |
| Ethylene | 0.0% | 0.0% | 0.0% | 5.6% | 0.0% | 23.0% | 15.7% | 9.2% |
| Propylene | 0.0% | 0.2% | 0.2% | 15.9% | 0.2% | 0.4% | 22.9% | 18.4% |
| Propane | 0.0% | 0.0% | 0.0% | 0.0% | 0.0% | 0.0% | 0.0% | 0.0% |
| 1-Butene | 0.0% | 2.3% | 2.3% | 2.3% | 2.3% | 1.8% | 2.6% | 2.4% |
| Isobutene | 0.0% | 3.9% | 3.9% | 4.8% | 3.9% | 3.0% | 3.0% | 4.2% |
| cis-2-butene | 35.0% | 14.5% | 14.5% | 2.3% | 14.5% | 11.1% | 2.6% | 2.4% |
| trans-2-butene | 35.0% | 15.1% | 15.1% | 2.7% | 15.1% | 11.6% | 3.1% | 2.9% |
| n-Butane | 30.0% | 63.9% | 63.9% | 63.9% | 63.9% | 49.1% | 49.1% | 58.6% |
| 1-Pentene | 0.0% | 0.0% | 0.0% | 0.1% | 0.0% | 0.0% | 0.0% | 0.1% |
| cis-2-Pentene | 0.0% | 0.0% | 0.0% | 0.2% | 0.0% | 0.0% | 0.3% | 0.2% |
| trans-2-Pentene | 0.0% | 0.0% | 0.0% | 0.3% | 0.0% | 0.0% | 0.6% | 0.4% |
| 2-Methy-2-butene | 0.0% | 0.0% | 0.0% | 0.8% | 0.0% | 0.0% | 0.0% | 0.5% |
| 3-Methy-1-butene | 0.0% | 0.0% | 0.0% | 0.1% | 0.0% | 0.0% | 0.0% | 0.1% |
| 2-Methy-1-butene | 0.0% | 0.0% | 0.0% | 0.4% | 0.0% | 0.0% | 0.0% | 0.3% |
| Sum of hexenes, hexanes, and heavier | 0.0% | 0.0% | 0.0% | 0.5% | 0.0% | 0.0% | 0.0% | 0.3% |
| Total mol % | 100.0% | 100.0% | 100.0% | 100.0% | 100.0% | 100.0% | 100.0% | 100.0% |

| Stream Number | 236 | 234 | 206 | 207 | 208 | 216 | 212 | 214 |
|---|---|---|---|---|---|---|---|---|
| Mole Flow, kmol/hr | 5.7 | 51.4 | 292.2 | 75.8 | 216.4 | 19.7 | 177.5 | 19.1 |
| Mass Flow, kg/hr | 161 | 1446 | 15757 | 3197 | 12561 | 1139 | 10248 | 1174 |
| Volumn Flow m$^3$/hr | 0.4 | 3.3 | 34.6 | 6.7 | 27.5 | 2.3 | 20.9 | 2.4 |
| Enthalpy, MW | 0.0 | 0.4 | −4.9 | 0.1 | −5.0 | −0.5 | −4.3 | −0.4 |
| MW, g/mol | 28.1 | 28.1 | 53.9 | 42.2 | 58.0 | 57.7 | 57.7 | 61.3 |
| Density, kg/m$^3$ | 438.1 | 438.1 | 455.8 | 477.9 | 456.5 | 490.8 | 490.8 | 495.8 |
| COMPONENTS, wt % | | | | | | | | |
| Ethylene | 99.0% | 99.0% | 0.1% | 0.3% | 0.0% | 0.0% | 0.0% | 0.0% |
| Propylene | 1.0% | 1.0% | 20.2% | 98.5% | 0.3% | 0.3% | 0.3% | 0.0% |
| Propane | 0.0% | 0.0% | 0.0% | 0.0% | 0.0% | 0.0% | 0.0% | 0.0% |
| 1-Butene | 0.0% | 0.0% | 2.6% | 0.3% | 3.2% | 3.6% | 3.6% | 0.2% |
| Isobutene | 0.0% | 0.0% | 4.6% | 0.6% | 5.6% | 6.1% | 6.1% | 0.3% |
| cis-2-butene | 0.0% | 0.0% | 2.6% | 0.0% | 3.3% | 3.1% | 3.1% | 5.2% |
| trans-2-butene | 0.0% | 0.0% | 3.2% | 0.0% | 4.0% | 4.1% | 4.1% | 3.0% |
| n-Butane | 0.0% | 0.0% | 64.6% | 0.3% | 81.0% | 82.7% | 82.7% | 63.7% |
| 1-Pentene | 0.0% | 0.0% | 0.1% | 0.0% | 0.1% | 0.0% | 0.0% | 1.1% |
| cis-2-Pentene | 0.0% | 0.0% | 0.2% | 0.0% | 0.3% | 0.0% | 0.0% | 3.1% |
| trans-2-Pentene | 0.0% | 0.0% | 0.5% | 0.0% | 0.6% | 0.0% | 0.0% | 6.1% |
| 2-Methy-2-butene | 0.0% | 0.0% | 0.6% | 0.0% | 0.7% | 0.0% | 0.0% | 7.3% |
| 3-Methy-1-butene | 0.0% | 0.0% | 0.1% | 0.0% | 0.1% | 0.0% | 0.0% | 0.7% |
| 2-Methy-1-butene | 0.0% | 0.0% | 0.3% | 0.0% | 0.4% | 0.0% | 0.0% | 3.8% |
| Sum of hexenes, hexanes, and heavier | 0.0% | 0.0% | 0.5% | 0.0% | 0.5% | 0.0% | 0.0% | 5.4% |
| Total mol % | 100.0% | 100.0% | 100.0% | 100.0% | 100.0% | 100.0% | 100.0% | 100.0% |

TABLE 2

| FIG. 1 with 100% efficiency in mol % | | | | | | | | |
|---|---|---|---|---|---|---|---|---|
| Stream Number | 210 | 201A/B/C/D | 201E | 232 | 201F | 238 | 240 | 203A/B |
| Mole Flow, kmol/hr | 100.0 | 277.5 | 194.3 | 214.7 | 83.3 | 134.6 | 134.6 | 349.3 |
| Mass Flow, kg/hr | 5670 | 15918 | 11143 | 11143 | 4775 | 6221 | 6221 | 17364 |
| Volumn Flow m³/hr | 6750 | 10562 | 7393 | 10556 | 3169 | 4199 | 9091 | 28.4 |
| Enthalpy, MW | 0.6 | −3.6 | −2.5 | −1.3 | −1.1 | −0.7 | 0.8 | −5.5 |
| MW, g/mol | 56.7 | 57.4 | 57.4 | 51.9 | 57.4 | 46.2 | 46.2 | 49.7 |
| Density, kg/m³ | 0.84 | 1.51 | 1.51 | 1.06 | 1.51 | 1.48 | 0.68 | 610.5 |
| COMPONENTS, mol % | | | | | | | | |
| Ethylene | 0.0% | 0.0% | 0.0% | 10.3% | 0.0% | 37.9% | 25.9% | 16.3% |
| Propylene | 0.0% | 0.2% | 0.2% | 19.6% | 0.2% | 0.4% | 25.1% | 21.7% |
| Propane | 0.0% | 0.0% | 0.0% | 0.0% | 0.0% | 0.0% | 0.0% | 0.0% |
| 1-Butene | 0.0% | 2.3% | 2.3% | 2.1% | 2.3% | 1.4% | 2.1% | 2.1% |
| Isobutene | 0.0% | 4.0% | 4.0% | 4.4% | 4.0% | 2.5% | 2.5% | 3.7% |
| cis-2-butene | 35.4% | 14.8% | 14.8% | 2.1% | 14.8% | 9.1% | 2.1% | 2.1% |
| trans-2-butene | 35.4% | 15.4% | 15.4% | 2.5% | 15.4% | 9.5% | 2.6% | 2.6% |
| n-Butane | 29.3% | 63.1% | 63.1% | 57.1% | 63.1% | 39.0% | 39.0% | 50.1% |
| 1-Pentene | 0.0% | 0.0% | 0.0% | 0.1% | 0.0% | 0.0% | 0.0% | 0.1% |
| cis-2-Pentene | 0.0% | 0.0% | 0.0% | 0.1% | 0.0% | 0.0% | 0.2% | 0.2% |
| trans-2-Pentene | 0.0% | 0.0% | 0.0% | 0.2% | 0.0% | 0.0% | 0.4% | 0.3% |
| 2-Methyl-2-butene | 0.0% | 0.0% | 0.0% | 0.6% | 0.0% | 0.0% | 0.0% | 0.4% |
| 3-Methyl-1-butene | 0.0% | 0.0% | 0.0% | 0.1% | 0.0% | 0.0% | 0.0% | 0.0% |
| 2-Methyl-1-butene | 0.0% | 0.0% | 0.0% | 0.3% | 0.0% | 0.0% | 0.0% | 0.2% |
| Sum of hexenes, hexanes, and heavier | 0.0% | 0.0% | 0.0% | 0.3% | 0.0% | 0.0% | 0.0% | 0.0% |
| Total mol % | 100.0% | 100.0% | 100.0% | 100.0% | 100.0% | 100.0% | 100.0% | 100.0% |
| Total mol % | 200% | 200% | 200% | 200% | 200% | 200% | 200% | 200% |

| Stream Number | 236 | 234 | 206 | 207 | 208 | 216 | 212 | 214 |
|---|---|---|---|---|---|---|---|---|
| Mole Flow, kmol/hr | 5.7 | 51.4 | 292.2 | 75.8 | 216.4 | 19.7 | 177.5 | 19.1 |
| Mass Flow, kg/hr | 161 | 1446 | 15757 | 3197 | 12561 | 1139 | 10248 | 1174 |
| Volumn Flow m³/hr | 0.4 | 3.3 | 34.6 | 6.7 | 27.5 | 2.3 | 20.9 | 2.4 |
| Enthalpy, MW | 0.0 | 0.4 | −4.9 | 0.1 | −5.0 | −0.5 | −4.3 | −0.4 |
| MW, g/mol | 28.1 | 28.1 | 53.9 | 42.2 | 58.0 | 57.7 | 57.7 | 61.3 |
| Density, kg/m³ | 438.1 | 438.1 | 455.8 | 477.9 | 456.5 | 490.8 | 490.8 | 495.8 |
| COMPONENTS, mol % | | | | | | | | |
| Ethylene | 99.3% | 99.3% | 0.1% | 0.4% | 0.0% | 0.0% | 0.0% | 0.0% |
| Propylene | 0.7% | 0.7% | 25.9% | 98.7% | 0.3% | 0.4% | 0.4% | 0.0% |
| Propane | 0.0% | 0.0% | 0.0% | 0.0% | 0.0% | 0.0% | 0.0% | 0.0% |
| 1-Butene | 0.0% | 0.0% | 2.5% | 0.2% | 3.4% | 3.7% | 3.7% | 0.2% |
| Isobutene | 0.0% | 0.0% | 4.4% | 0.5% | 5.8% | 6.3% | 6.3% | 0.3% |
| cis-2-butene | 0.0% | 0.0% | 2.5% | 0.0% | 3.4% | 3.2% | 3.2% | 5.6% |
| trans-2-butene | 0.0% | 0.0% | 3.1% | 0.0% | 4.1% | 4.2% | 4.2% | 3.2% |
| n-Butane | 0.0% | 0.0% | 59.9% | 0.2% | 80.8% | 82.2% | 82.2% | 67.2% |
| 1-Pentene | 0.0% | 0.0% | 0.1% | 0.0% | 0.1% | 0.0% | 0.0% | 1.0% |
| cis-2-Pentene | 0.0% | 0.0% | 0.2% | 0.0% | 0.2% | 0.0% | 0.0% | 2.7% |
| trans-2-Pentene | 0.0% | 0.0% | 0.4% | 0.0% | 0.5% | 0.0% | 0.0% | 5.4% |
| 2-Methyl-2-butene | 0.0% | 0.0% | 0.4% | 0.0% | 0.6% | 0.0% | 0.0% | 6.4% |
| 3-Methyl-1-butene | 0.0% | 0.0% | 0.1% | 0.0% | 0.1% | 0.0% | 0.0% | 0.6% |
| 2-Methyl-1-butene | 0.0% | 0.0% | 0.2% | 0.0% | 0.3% | 0.0% | 0.0% | 3.3% |
| Sum of hexenes, hexanes, and heavier | 0.0% | 0.0% | 0.1% | 0.0% | 0.3% | 0.0% | 0.0% | 3.8% |
| Total mol % | 100.0% | 100.0% | 100.0% | 100.0% | 100.0% | 100.0% | 100.0% | 100.0% |

TABLE 3

| | FIG. 1 with 80% efficiency in wt. % | | | | | | | |
|---|---|---|---|---|---|---|---|---|
| Stream Number | 210 | 201A | 201E | 232 | 201F | 238 | 240 | 203A/B |
| Mole Flow, kmol/hr | 100.0 | 322.4 | 225.7 | 151.6 | 96.7 | 121.3 | 151.6 | 396.8 |
| Mass Flow, kg/hr | 5669.7 | 18487.7 | 12941.4 | 7091.3 | 5546.3 | 5673.0 | 7091.3 | 20032.7 |
| Volumn Flow m³/hr | 6749.8 | 11369.4 | 7958.6 | 9280.6 | 3410.8 | 3526.3 | 9280.6 | 32.6 |
| Enthalpy, MW | 0.6 | −4.4 | −3.1 | 0.6 | −1.3 | −0.7 | 0.6 | −6.4 |
| MW, g/mol | 56.7 | 57.3 | 57.3 | 46.8 | 57.3 | 46.8 | 46.8 | 50.5 |
| Density, kg/m³ | 0.84 | 1.63 | 1.63 | 0.76 | 1.63 | 1.61 | 0.76 | 614.74 |
| COMPONENTS, mol % | | | | | | | | |
| Ethylene | 0.0% | 0.0% | 0.0% | 26.2% | 0.0% | 36.0% | 26.2% | 15.3% |
| Propylene | 0.0% | 0.2% | 0.2% | 20.5% | 0.2% | 0.4% | 20.5% | 18.0% |
| Propane | 0.0% | 0.0% | 0.0% | 0.0% | 0.0% | 0.0% | 0.0% | 0.0% |
| 1-Butene | 0.0% | 2.4% | 2.4% | 2.2% | 2.4% | 1.5% | 2.2% | 2.2% |
| Isobutene | 0.0% | 4.0% | 4.0% | 2.6% | 4.0% | 2.6% | 2.6% | 3.7% |
| cis-2-butene | 35.4% | 15.2% | 15.2% | 3.8% | 15.2% | 9.7% | 3.8% | 4.3% |
| trans-2-butene | 35.4% | 16.0% | 16.0% | 4.4% | 16.0% | 10.2% | 4.4% | 4.8% |
| n-Butane | 29.3% | 62.1% | 62.1% | 39.6% | 62.1% | 39.6% | 39.6% | 50.5% |
| 1-Pentene | 0.0% | 0.0% | 0.0% | 0.0% | 0.0% | 0.0% | 0.0% | 0.1% |
| cis-2-Pentene | 0.0% | 0.0% | 0.0% | 0.2% | 0.0% | 0.0% | 0.2% | 0.1% |
| trans-2-Pentene | 0.0% | 0.0% | 0.0% | 0.4% | 0.0% | 0.0% | 0.4% | 0.3% |
| 2-Methyl-2-butene | 0.0% | 0.0% | 0.0% | 0.0% | 0.0% | 0.0% | 0.0% | 0.3% |
| 3-Methyl-1-butene | 0.0% | 0.0% | 0.0% | 0.0% | 0.0% | 0.0% | 0.0% | 0.0% |
| 2-Methyl-1-butene | 0.0% | 0.0% | 0.0% | 0.0% | 0.0% | 0.0% | 0.0% | 0.2% |
| Sum of hexenes, hexanes, and heavier | 0.0% | 0.0% | 0.0% | 0.0% | 0.0% | 0.0% | 0.0% | 0.0% |
| Total mol % | 100.0% | 100.0% | 100.0% | 100.0% | 100.0% | 100.0% | 100.0% | 100.0% |
| Stream Number | 236 | 234 | 206 | 207 | 208 | 216 | 212 | 214 |
| Mole Flow, kmol/hr | 6.1 | 54.9 | 335.8 | 71.2 | 264.6 | 24.7 | 222.4 | 17.5 |
| Mass Flow, kg/hr | 171.7 | 1545.0 | 18316.1 | 3000.8 | 15315.3 | 1424.2 | 12818.0 | 1073.1 |
| Volumn Flow m³/hr | 0.4 | 3.5 | 40.3 | 6.3 | 33.4 | 2.9 | 26.0 | 2.2 |
| Enthalpy, MW | 0.0 | 0.4 | −5.7 | 0.1 | −5.8 | −0.6 | −5.1 | −0.3 |
| MW, g/mol | 28.1 | 28.1 | 54.5 | 42.2 | 57.9 | 57.6 | 57.6 | 61.4 |
| Density, kg/m³ | 438.07 | 438.09 | 454.35 | 477.91 | 457.93 | 492.34 | 492.34 | 498.92 |
| COMPONENTS, mol % | | | | | | | | |
| Ethylene | 99.3% | 99.3% | 0.1% | 0.4% | 0.0% | 0.0% | 0.0% | 0.0% |
| Propylene | 0.7% | 0.7% | 21.1% | 98.7% | 0.3% | 0.3% | 0.3% | 0.0% |
| Propane | 0.0% | 0.0% | 0.0% | 0.0% | 0.0% | 0.0% | 0.0% | 0.0% |
| 1-Butene | 0.0% | 0.0% | 2.6% | 0.2% | 3.3% | 3.5% | 3.5% | 0.2% |
| Isobutene | 0.0% | 0.0% | 4.4% | 0.4% | 5.5% | 5.8% | 5.8% | 0.2% |
| cis-2-butene | 0.0% | 0.0% | 5.1% | 0.0% | 6.4% | 6.1% | 6.1% | 11.3% |
| trans-2-butene | 0.0% | 0.0% | 5.7% | 0.0% | 7.2% | 7.3% | 7.3% | 5.2% |
| n-Butane | 0.0% | 0.0% | 59.7% | 0.2% | 75.7% | 76.9% | 76.9% | 57.8% |
| 1-Pentene | 0.0% | 0.0% | 0.1% | 0.0% | 0.1% | 0.0% | 0.0% | 1.0% |
| cis-2-Pentene | 0.0% | 0.0% | 0.2% | 0.0% | 0.2% | 0.0% | 0.0% | 3.1% |
| trans-2-Pentene | 0.0% | 0.0% | 0.3% | 0.0% | 0.4% | 0.0% | 0.0% | 6.1% |
| 2-Methyl-2-butene | 0.0% | 0.0% | 0.4% | 0.0% | 0.4% | 0.0% | 0.0% | 6.7% |
| 3-Methyl-1-butene | 0.0% | 0.0% | 0.1% | 0.0% | 0.1% | 0.0% | 0.0% | 0.7% |
| 2-Methyl-1-butene | 0.0% | 0.0% | 0.2% | 0.0% | 0.3% | 0.0% | 0.0% | 3.5% |
| Sum of hexenes, hexanes, and heavier | 0.0% | 0.0% | 0.0% | 0.0% | 0.1% | 0.0% | 0.0% | 4.1% |
| Total mol % | 100.0% | 100.0% | 100.0% | 100.0% | 100.0% | 100.0% | 100.0% | 100.0% |

TABLE 4

| | FIG. 1 with 80% efficiency in mol % | | | | | | | |
|---|---|---|---|---|---|---|---|---|
| Stream Number | 210 | 201A | 201E | 232 | 201F | 238 | 240 | 203A/B |
| Mole Flow, kmol/hr | 100.0 | 322.4 | 225.7 | 151.6 | 96.7 | 121.3 | 151.6 | 396.8 |
| Mass Flow, kg/hr | 5669.7 | 18487.7 | 12941.4 | 7091.3 | 5546.3 | 5673.0 | 7091.3 | 20032.7 |
| Volumn Flow m³/hr | 6749.8 | 11369.4 | 7958.6 | 9280.6 | 3410.8 | 3526.3 | 9280.6 | 32.6 |
| Enthalpy, MW | 0.6 | −4.4 | −3.1 | 0.6 | −1.3 | −0.7 | 0.6 | −6.4 |
| MW, g/mol | 56.7 | 57.3 | 57.3 | 46.8 | 57.3 | 46.8 | 46.8 | 50.5 |
| Density, kg/m³ | 0.84 | 1.63 | 1.63 | 0.76 | 1.63 | 1.61 | 0.76 | 614.74 |
| COMPONENTS, wt % | | | | | | | | |
| Ethylene | 0.0% | 0.0% | 0.0% | 15.7% | 0.0% | 21.6% | 15.7% | 8.5% |
| Propylene | 0.0% | 0.1% | 0.1% | 18.4% | 0.1% | 0.3% | 18.4% | 15.0% |
| Propane | 0.0% | 0.0% | 0.0% | 0.0% | 0.0% | 0.0% | 0.0% | 0.0% |
| 1-Butene | 0.0% | 2.4% | 2.4% | 2.7% | 2.4% | 1.8% | 2.7% | 2.5% |
| Isobutene | 0.0% | 3.9% | 3.9% | 3.1% | 3.9% | 3.1% | 3.1% | 4.1% |
| cis-2-butene | 35.0% | 14.8% | 14.8% | 4.6% | 14.8% | 11.6% | 4.6% | 4.8% |
| trans-2-butene | 35.0% | 15.7% | 15.7% | 5.2% | 15.7% | 12.3% | 5.2% | 5.3% |
| n-Butane | 30.0% | 63.0% | 63.0% | 49.3% | 63.0% | 49.3% | 49.3% | 58.1% |
| 1-Pentene | 0.0% | 0.0% | 0.0% | 0.0% | 0.0% | 0.0% | 0.0% | 0.1% |
| cis-2-Pentene | 0.0% | 0.0% | 0.0% | 0.3% | 0.0% | 0.0% | 0.3% | 0.2% |
| trans-2-Pentene | 0.0% | 0.0% | 0.0% | 0.6% | 0.0% | 0.0% | 0.6% | 0.4% |
| 2-Methy-2-butene | 0.0% | 0.0% | 0.0% | 0.0% | 0.0% | 0.0% | 0.0% | 0.4% |
| 3-Methy-1-butene | 0.0% | 0.0% | 0.0% | 0.0% | 0.0% | 0.0% | 0.0% | 0.1% |
| 2-Methy-1-butene | 0.0% | 0.0% | 0.0% | 0.0% | 0.0% | 0.0% | 0.0% | 0.2% |
| Sum of hexenes, hexanes, and heavier | 0.0% | 0.0% | 0.0% | 0.0% | 0.0% | 0.0% | 0.0% | 0.3% |
| Total mol % | 100.0% | 100.0% | 100.0% | 100.0% | 100.0% | 100.0% | 100.0% | 100.0% |

| Stream Number | 236 | 234 | 206 | 207 | 208 | 216 | 212 | 214 |
|---|---|---|---|---|---|---|---|---|
| Mole Flow, kmol/hr | 6.1 | 54.9 | 335.8 | 71.2 | 264.6 | 24.7 | 222.4 | 17.5 |
| Mass Flow, kg/hr | 171.7 | 1545.0 | 18316.1 | 3000.8 | 15315.3 | 1424.2 | 12818.0 | 1073.1 |
| Volumn Flow m³/hr | 0.4 | 3.5 | 40.3 | 6.3 | 33.4 | 2.9 | 26.0 | 2.2 |
| Enthalpy, MW | 0.0 | 0.4 | −5.7 | 0.1 | −5.8 | −0.6 | −5.1 | −0.3 |
| MW, g/mol | 28.1 | 28.1 | 54.5 | 42.2 | 57.9 | 57.6 | 57.6 | 61.4 |
| Density, kg/m³ | 438.07 | 438.09 | 454.35 | 477.91 | 457.93 | 492.34 | 492.34 | 498.92 |
| COMPONENTS, wt % | | | | | | | | |
| Ethylene | 99.0% | 99.0% | 0.0% | 0.3% | 0.0% | 0.0% | 0.0% | 0.0% |
| Propylene | 1.0% | 1.0% | 16.3% | 98.5% | 0.2% | 0.2% | 0.2% | 0.0% |
| Propane | 0.0% | 0.0% | 0.0% | 0.0% | 0.0% | 0.0% | 0.0% | 0.0% |
| 1-Butene | 0.0% | 0.0% | 2.7% | 0.3% | 3.2% | 3.4% | 3.4% | 0.1% |
| Isobutene | 0.0% | 0.0% | 4.5% | 0.6% | 5.3% | 5.7% | 5.7% | 0.2% |
| cis-2-butene | 0.0% | 0.0% | 5.2% | 0.0% | 6.2% | 5.9% | 5.9% | 10.4% |
| trans-2-butene | 0.0% | 0.0% | 5.8% | 0.0% | 7.0% | 7.1% | 7.1% | 4.7% |
| n-Butane | 0.0% | 0.0% | 63.6% | 0.3% | 76.0% | 77.6% | 77.6% | 54.7% |
| 1-Pentene | 0.0% | 0.0% | 0.1% | 0.0% | 0.1% | 0.0% | 0.0% | 1.2% |
| cis-2-Pentene | 0.0% | 0.0% | 0.2% | 0.0% | 0.3% | 0.0% | 0.0% | 3.6% |
| trans-2-Pentene | 0.0% | 0.0% | 0.4% | 0.0% | 0.5% | 0.0% | 0.0% | 7.0% |
| 2-Methy-2-butene | 0.0% | 0.0% | 0.5% | 0.0% | 0.5% | 0.0% | 0.0% | 7.7% |
| 3-Methy-1-butene | 0.0% | 0.0% | 0.1% | 0.0% | 0.1% | 0.0% | 0.0% | 0.8% |
| 2-Methy-1-butene | 0.0% | 0.0% | 0.3% | 0.0% | 0.3% | 0.0% | 0.0% | 4.0% |
| Sum of hexenes, hexanes, and heavier | 0.0% | 0.0% | 0.3% | 0.0% | 0.5% | 0.0% | 0.0% | 5.9% |
| Total mol % | 100.0% | 100.0% | 100.0% | 100.0% | 100.0% | 100.0% | 100.0% | 100.0% |

Example 2

Figure 4:
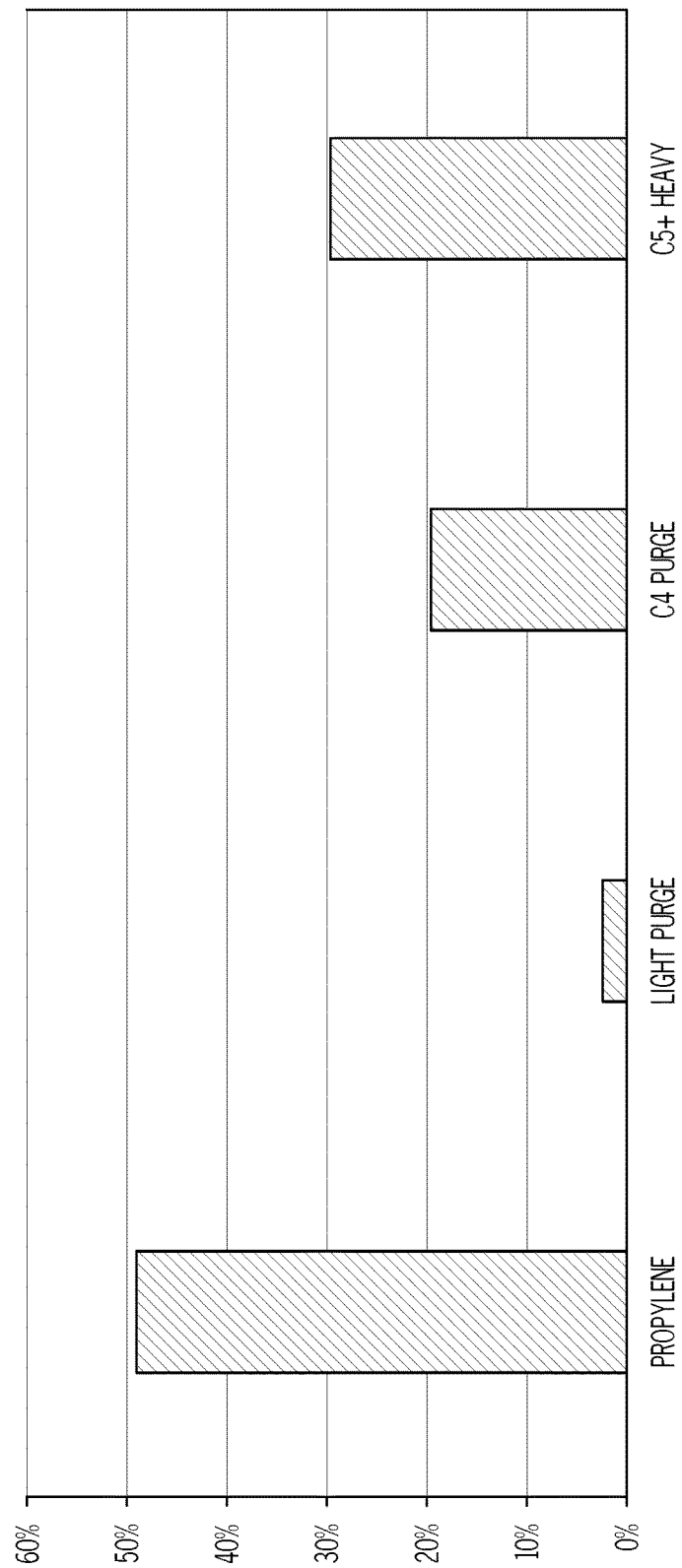
FIG. 4 depicts a bar graph displaying the product distribution (in wt. %) of the system of FIG. 2, according to one or more embodiments described in this disclosure.

The systems of FIG. 2 was also computer modeled using Aspen Plus®. The subsequent tables (Tables 9-16) depict the stream compositions and flowrates, as well as thermal properties for selected streams. The system inlet stream composition and catalyst reaction rates used for the model were the same as those of Example 1. The system inlet stream of 35 wt. % cis-2-butene, 35 wt. % trans-2-butene, and 30 wt. % n-butane was used for the model. The stream numbers corresponds with the stream or stream segment shown in FIG. 2. Simulations were run for 100% efficiency and 80% efficiency. Additionally, data is provided on a weight basis and a mole basis for each simulation. Table 5 depicts data for a simulation of the system of FIG. 2 with 100% efficiency and shows components on a mass basis. Table 6 depicts data for a simulation of the system of FIG. 2 with 100% efficiency and shows components on a mole basis. Table 7 depicts data for a simulation of the system of FIG. 2 with 80% efficiency and shows components on a mass basis. Table 8 depicts data for a simulation of the system of FIG. 2 with 80% efficiency and shows components on a mole basis. Additionally, FIG. 4 depicts a bar graph displaying the product distribution of the system of FIG. 2 as shown in Table 5 where, on the bar graph, "Propylene" corresponds with the stream of transfer line 307, "Light Purge" corresponds with the stream of transfer line 336, "C4 Purge" corresponds with the stream of transfer line 316, and "C5+ Heavy" corresponds with the stream of transfer line 314.

TABLE 5

FIG. 2 with 100% efficiency in wt. %

| Stream Number | 301A/B/C/D | 301E | 332 | 301F | 338 | 340 | 303A/B |
|---|---|---|---|---|---|---|---|
| Mole Flow, kmol/hr | 100.0 | 85.0 | 102.2 | 15.0 | 225.8 | 225.8 | 328.0 |
| Mass Flow, kg/hr | 5670 | 4819 | 4819 | 850 | 11831 | 11831 | 16650 |
| Volumn Flow $m^3$/hr | 6750 | 5737 | 6901 | 1012 | 3966 | 15244 | 26.9 |
| Enthalpy, MW | 0.6 | 0.5 | 0.9 | 0.1 | −2.7 | 0.8 | −4.5 |
| MW, g/mol | 56.7 | 56.7 | 47.2 | 56.7 | 52.4 | 52.4 | 50.8 |
| Density, kg/$m^3$ | 0.84 | 0.84 | 0.70 | 0.84 | 2.98 | 0.78 | 619.0 |
| COMPONENTS, wt % | | | | | | | |
| Ethylene | 0.0% | 0.0% | 10.8% | 0.0% | 8.7% | 5.3% | 6.9% |
| Propylene | 0.0% | 0.0% | 30.9% | 0.0% | 0.3% | 11.1% | 16.8% |
| Propane | 0.0% | 0.0% | 0.0% | 0.0% | 0.0% | 0.0% | 0.0% |
| 1-Butene | 0.0% | 0.0% | 4.4% | 0.0% | 3.2% | 1.8% | 2.6% |
| Isobutene | 0.0% | 0.0% | 9.3% | 0.0% | 28.0% | 28.0% | 22.5% |
| cis-2-butene | 35.0% | 35.0% | 4.4% | 35.0% | 5.0% | 1.8% | 2.5% |
| trans-2-butene | 35.0% | 35.0% | 5.3% | 35.0% | 5.8% | 2.2% | 3.1% |
| n-Butane | 30.0% | 30.0% | 30.0% | 30.0% | 48.9% | 48.9% | 43.5% |
| 1-Pentene | 0.0% | 0.0% | 0.2% | 0.0% | 0.0% | 0.0% | 0.1% |
| cis-2-Pentene | 0.0% | 0.0% | 0.3% | 0.0% | 0.0% | 0.3% | 0.3% |
| trans-2-Pentene | 0.0% | 0.0% | 0.6% | 0.0% | 0.0% | 0.6% | 0.6% |
| 2-Methy-2-butene | 0.0% | 0.0% | 1.5% | 0.0% | 0.0% | 0.0% | 0.4% |
| 3-Methy-1-butene | 0.0% | 0.0% | 0.2% | 0.0% | 0.0% | 0.0% | 0.1% |
| 2-Methy-1-butene | 0.0% | 0.0% | 0.8% | 0.0% | 0.0% | 0.0% | 0.3% |
| Sum of hexenes, hexanes, and heavier | 0.0% | 0.0% | 1.1% | 0.0% | 0.0% | 0.0% | 0.3% |
| Total mol % | 100.0% | 100.0% | 100.0% | 100.0% | 100.0% | 100.0% | 100.0% |

| Stream Number | 336 | 334 | 306 | 307 | 308 | 316 | 312A/B | 314 |
|---|---|---|---|---|---|---|---|---|
| Mole Flow, kmol/hr | 4.1 | 37.0 | 286.9 | 65.9 | 221.1 | 19.3 | 173.8 | 27.9 |
| Mass Flow, kg/hr | 116 | 1040 | 15494 | 2771 | 12723 | 1104 | 9940 | 1679 |
| Volumn Flow $m^3$/hr | 0.3 | 2.4 | 33.8 | 5.8 | 27.5 | 2.2 | 20.0 | 3.4 |
| Enthalpy, MW | 0.0 | 0.3 | −3.8 | 0.1 | −3.9 | −0.3 | −3.1 | −0.6 |
| MW, g/mol | 28.1 | 28.1 | 54.0 | 42.1 | 57.6 | 57.2 | 57.2 | 60.1 |
| Density, kg/$m^3$ | 438.1 | 438.1 | 458.0 | 477.4 | 462.2 | 497.0 | 497.0 | 494.5 |
| COMPONENTS, wt % | | | | | | | | |
| Ethylene | 99.0% | 99.0% | 0.0% | 0.2% | 0.0% | 0.0% | 0.0% | 0.0% |
| Propylene | 1.0% | 1.0% | 18.0% | 99.5% | 0.2% | 0.3% | 0.3% | 0.0% |
| Propane | 0.0% | 0.0% | 0.0% | 0.0% | 0.0% | 0.0% | 0.0% | 0.0% |
| 1-Butene | 0.0% | 0.0% | 2.7% | 0.0% | 3.3% | 3.8% | 3.8% | 0.6% |
| Isobutene | 0.0% | 0.0% | 24.2% | 0.3% | 29.5% | 33.3% | 33.3% | 4.3% |
| cis-2-butene | 0.0% | 0.0% | 2.7% | 0.0% | 3.3% | 3.0% | 3.0% | 5.8% |
| trans-2-butene | 0.0% | 0.0% | 3.3% | 0.0% | 4.0% | 4.0% | 4.0% | 4.5% |
| n-Butane | 0.0% | 0.0% | 46.7% | 0.0% | 56.9% | 55.7% | 55.7% | 64.7% |

TABLE 5-continued

| FIG. 2 with 100% efficiency in wt. % | | | | | | | | |
|---|---|---|---|---|---|---|---|---|
| 1-Pentene | 0.0% | 0.0% | 0.1% | 0.0% | 0.1% | 0.0% | 0.0% | 0.7% |
| cis-2-Pentene | 0.0% | 0.0% | 0.3% | 0.0% | 0.4% | 0.0% | 0.0% | 3.0% |
| trans-2-Pentene | 0.0% | 0.0% | 0.7% | 0.0% | 0.8% | 0.0% | 0.0% | 5.9% |
| 2-Methy-2-butene | 0.0% | 0.0% | 0.5% | 0.0% | 0.6% | 0.0% | 0.0% | 4.3% |
| 3-Methy-1-butene | 0.0% | 0.0% | 0.1% | 0.0% | 0.1% | 0.0% | 0.0% | 0.5% |
| 2-Methy-1-butene | 0.0% | 0.0% | 0.3% | 0.0% | 0.3% | 0.0% | 0.0% | 2.4% |
| Sum of hexenes, hexanes, and heavier | 0.0% | 0.0% | 0.3% | 0.0% | 0.5% | 0.0% | 0.0% | 3.4% |
| Total mol % | 100.0% | 100.0% | 100.0% | 100.0% | 100.0% | 100.0% | 100.0% | 100.0% |

TABLE 6

| FIG. 2 with 100% efficiency in mol % | | | | | | | |
|---|---|---|---|---|---|---|---|
| Stream Number | 301A | 301E | 332 | 301F | 338 | 340 | 303A/B |
| Mole Flow, kmol/hr | 100.0 | 85.0 | 102.2 | 15.0 | 225.8 | 225.8 | 328.0 |
| Mass Flow, kg/hr | 5670 | 4819 | 4819 | 850 | 11831 | 11831 | 16650 |
| Volumn Flow m³/hr | 6750 | 5737 | 6901 | 1012 | 3966 | 15244 | 26.9 |
| Enthalpy, MW | 0.6 | 0.5 | 0.9 | 0.1 | −2.7 | 0.8 | −4.5 |
| MW, g/mol | 56.7 | 56.7 | 47.2 | 56.7 | 52.4 | 52.4 | 50.8 |
| Density, kg/m³ | 0.84 | 0.84 | 0.70 | 0.84 | 2.98 | 0.78 | 619.0 |
| COMPONENTS, mol % | | | | | | | |
| Ethylene | 0.0% | 0.0% | 18.2% | 0.0% | 16.3% | 9.9% | 12.5% |
| Propylene | 0.0% | 0.0% | 34.6% | 0.0% | 0.4% | 13.8% | 20.3% |
| Propane | 0.0% | 0.0% | 0.0% | 0.0% | 0.0% | 0.0% | 0.0% |
| 1-Butene | 0.0% | 0.0% | 3.7% | 0.0% | 2.9% | 1.7% | 2.3% |
| Isobutene | 0.0% | 0.0% | 7.8% | 0.0% | 26.1% | 26.1% | 20.4% |
| cis-2-butene | 35.4% | 35.4% | 3.7% | 35.4% | 4.7% | 1.7% | 2.3% |
| trans-2-butene | 35.4% | 35.4% | 4.5% | 35.4% | 5.5% | 2.0% | 2.8% |
| n-Butane | 29.3% | 29.3% | 24.3% | 29.3% | 44.1% | 44.1% | 37.9% |
| 1-Pentene | 0.0% | 0.0% | 0.2% | 0.0% | 0.0% | 0.0% | 0.1% |
| cis-2-Pentene | 0.0% | 0.0% | 0.2% | 0.0% | 0.0% | 0.2% | 0.2% |
| trans-2-Pentene | 0.0% | 0.0% | 0.4% | 0.0% | 0.0% | 0.5% | 0.4% |
| 2-Methyl-2-butene | 0.0% | 0.0% | 1.0% | 0.0% | 0.0% | 0.0% | 0.3% |
| 3-Methyl-1-butene | 0.0% | 0.0% | 0.1% | 0.0% | 0.0% | 0.0% | 0.1% |
| 2-Methyl-1-butene | 0.0% | 0.0% | 0.6% | 0.0% | 0.0% | 0.0% | 0.2% |
| Sum of hexenes, hexanes, and heavier | 0.0% | 0.0% | 0.6% | 0.0% | 0.0% | 0.0% | 0.0% |
| Total mol % | 100.0% | 100.0% | 100.0% | 100.0% | 100.0% | 100.0% | 100.0% |
| Stream Number | 336 | 334 | 306 | 307 | 308 | 316 | 312A/B | 314 |
| Mole Flow, kmol/hr | 4.1 | 37.0 | 286.9 | 65.9 | 221.1 | 19.3 | 173.8 | 27.9 |
| Mass Flow, kg/hr | 116 | 1040 | 15494 | 2771 | 12723 | 1104 | 9940 | 1679 |
| Volumn Flow m³/hr | 0.3 | 2.4 | 33.8 | 5.8 | 27.5 | 2.2 | 20.0 | 3.4 |
| Enthalpy, MW | 0.0 | 0.3 | −3.8 | 0.1 | −3.9 | −0.3 | −3.1 | −0.6 |
| MW, g/mol | 28.1 | 28.1 | 54.0 | 42.1 | 57.6 | 57.2 | 57.2 | 60.1 |
| Density, kg/m³ | 438.1 | 438.1 | 458.0 | 477.4 | 462.2 | 497.0 | 497.0 | 494.5 |
| COMPONENTS, mol % | | | | | | | | |
| Ethylene | 99.3% | 99.3% | 0.1% | 0.3% | 0.0% | 0.0% | 0.0% | 0.0% |
| Propylene | 0.7% | 0.7% | 23.1% | 99.5% | 0.3% | 0.3% | 0.3% | 0.0% |
| Propane | 0.0% | 0.0% | 0.0% | 0.0% | 0.0% | 0.0% | 0.0% | 0.0% |
| 1-Butene | 0.0% | 0.0% | 2.6% | 0.0% | 3.4% | 3.8% | 3.8% | 0.6% |
| Isobutene | 0.0% | 0.0% | 23.3% | 0.2% | 30.2% | 33.9% | 33.9% | 4.6% |

TABLE 6-continued

FIG. 2 with 100% efficiency in mol %

|  |  |  |  |  |  |  |  |
|---|---|---|---|---|---|---|---|
| cis-2-butene | 0.0% | 0.0% | 2.6% | 0.0% | 3.4% | 3.0% | 3.0% | 6.2% |
| trans-2-butene | 0.0% | 0.0% | 3.2% | 0.0% | 4.1% | 4.0% | 4.0% | 4.8% |
| n-Butane | 0.0% | 0.0% | 43.4% | 0.0% | 56.3% | 54.8% | 54.8% | 66.9% |
| 1-Pentene | 0.0% | 0.0% | 0.1% | 0.0% | 0.1% | 0.0% | 0.0% | 0.6% |
| cis-2-Pentene | 0.0% | 0.0% | 0.3% | 0.0% | 0.3% | 0.0% | 0.0% | 2.6% |
| trans-2-Pentene | 0.0% | 0.0% | 0.5% | 0.0% | 0.7% | 0.0% | 0.0% | 5.0% |
| 2-Methyl-2-butene | 0.0% | 0.0% | 0.4% | 0.0% | 0.5% | 0.0% | 0.0% | 3.7% |
| 3-Methyl-1-butene | 0.0% | 0.0% | 0.1% | 0.0% | 0.1% | 0.0% | 0.0% | 0.5% |
| 2-Methyl-1-butene | 0.0% | 0.0% | 0.2% | 0.0% | 0.3% | 0.0% | 0.0% | 2.0% |
| Sum of hexenes, hexanes, and heavier | 0.0% | 0.0% | 0.0% | 0.0% | 0.3% | 0.0% | 0.0% | 2.4% |
| Total mol % | 100.0% | 100.0% | 100.0% | 100.0% | 100.0% | 100.0% | 100.0% | 100.0% |

TABLE 7

FIG. 2 with 80% efficiency in wt. %

| Stream Number | 301A | 301E | 332 | 301F | 338 | 340 | 303A/B |
|---|---|---|---|---|---|---|---|
| Mole Flow, kmol/hr | 100.0 | 85.0 | 98.8 | 15.0 | 275.6 | 275.6 | 374.4 |
| Mass Flow, kg/hr | 5670 | 4819 | 4819 | 850 | 14943 | 14943 | 19762 |
| Volumn Flow m³/hr | 6750 | 5737 | 6668 | 1012 | 4605 | 16513 | 31.5 |
| Enthalpy, MW | 0.6 | 0.5 | 0.9 | 0.1 | −4.0 | −0.3 | −6.0 |
| MW, g/mol | 56.7 | 56.7 | 48.8 | 56.7 | 54.2 | 54.2 | 52.8 |
| Density, kg/m³ | 0.84 | 0.84 | 0.72 | 0.84 | 3.24 | 0.90 | 627.5 |
| COMPONENTS, wt % |  |  |  |  |  |  |  |
| Ethylene | 0.0% | 0.0% | 8.7% | 0.0% | 5.3% | 3.2% | 4.5% |
| Propylene | 0.0% | 0.0% | 24.7% | 0.0% | 0.2% | 8.2% | 12.3% |
| Propane | 0.0% | 0.0% | 0.0% | 0.0% | 0.0% | 0.0% | 0.0% |
| 1-Butene | 0.0% | 0.0% | 3.5% | 0.0% | 4.0% | 3.3% | 3.4% |
| Isobutene | 0.0% | 0.0% | 7.4% | 0.0% | 22.4% | 19.9% | 16.8% |
| cis-2-butene | 35.0% | 35.0% | 10.5% | 35.0% | 7.5% | 4.0% | 5.6% |
| trans-2-butene | 35.0% | 35.0% | 11.3% | 35.0% | 9.0% | 4.8% | 6.4% |
| n-Butane | 30.0% | 30.0% | 30.0% | 30.0% | 54.0% | 54.0% | 48.1% |
| 1-Pentene | 0.0% | 0.0% | 0.2% | 0.0% | 0.0% | 0.0% | 0.1% |
| cis-2-Pentene | 0.0% | 0.0% | 0.3% | 0.0% | 0.0% | 0.8% | 0.7% |
| trans-2-Pentene | 0.0% | 0.0% | 0.5% | 0.0% | 0.1% | 1.6% | 1.3% |
| 2-Methy-2-butene | 0.0% | 0.0% | 1.2% | 0.0% | 0.0% | 0.0% | 0.3% |
| 3-Methy-1-butene | 0.0% | 0.0% | 0.2% | 0.0% | 0.0% | 0.0% | 0.1% |
| 2-Methy-1-butene | 0.0% | 0.0% | 0.7% | 0.0% | 0.0% | 0.0% | 0.2% |
| Sum of hexenes, hexanes, and heavier | 0.0% | 0.0% | 1.0% | 0.0% | 0.0% | 0.1% | 0.1% |
| Total mol % | 100.0% | 100.0% | 100.0% | 100.0% | 100.0% | 100.0% | 100.0% |

| Stream Number | 336 | 334 | 306 | 307 | 308 | 316 | 312A/B | 314 |
|---|---|---|---|---|---|---|---|---|
| Mole Flow, kmol/hr | 3.2 | 28.6 | 342.6 | 57.1 | 285.5 | 25.8 | 232.1 | 27.7 |
| Mass Flow, kg/hr | 89 | 805 | 18868 | 2402 | 16466 | 1476 | 13288 | 1702 |
| Volumn Flow m³/hr | 0.2 | 1.8 | 41.4 | 5.0 | 35.6 | 3.0 | 26.8 | 3.4 |
| Enthalpy, MW | 0.0 | 0.2 | −5.0 | 0.1 | −5.1 | −0.5 | −4.3 | −0.5 |
| MW, g/mol | 28.1 | 28.1 | 55.1 | 42.1 | 57.7 | 57.3 | 57.3 | 61.4 |
| Density, kg/m³ | 438.1 | 438.1 | 455.3 | 477.4 | 462.5 | 496.7 | 496.7 | 500.3 |
| COMPONENTS, wt % |  |  |  |  |  |  |  |  |
| Ethylene | 99.0% | 99.0% | 0.0% | 0.2% | 0.0% | 0.0% | 0.0% | 0.0% |
| Propylene | 1.0% | 1.0% | 12.8% | 99.5% | 0.1% | 0.2% | 0.2% | 0.0% |

TABLE 7-continued

| FIG. 2 with 80% efficiency in wt. % | | | | | | | | |
|---|---|---|---|---|---|---|---|---|
| Propane | 0.0% | 0.0% | 0.0% | 0.0% | 0.0% | 0.0% | 0.0% | 0.0% |
| 1-Butene | 0.0% | 0.0% | 3.5% | 0.0% | 4.0% | 4.5% | 4.5% | 0.3% |
| Isobutene | 0.0% | 0.0% | 17.6% | 0.3% | 20.2% | 22.4% | 22.4% | 1.3% |
| cis-2-butene | 0.0% | 0.0% | 5.9% | 0.0% | 6.7% | 6.2% | 6.2% | 10.8% |
| trans-2-butene | 0.0% | 0.0% | 6.7% | 0.0% | 7.7% | 7.8% | 7.8% | 6.3% |
| n-Butane | 0.0% | 0.0% | 50.4% | 0.0% | 57.7% | 58.8% | 58.8% | 49.0% |
| 1-Pentene | 0.0% | 0.0% | 0.1% | 0.0% | 0.1% | 0.0% | 0.0% | 0.5% |
| cis-2-Pentene | 0.0% | 0.0% | 0.7% | 0.0% | 0.8% | 0.0% | 0.0% | 7.6% |
| trans-2-Pentene | 0.0% | 0.0% | 1.4% | 0.0% | 1.6% | 0.1% | 0.1% | 15.0% |
| 2-Methy-2-butene | 0.0% | 0.0% | 0.3% | 0.0% | 0.4% | 0.0% | 0.0% | 3.4% |
| 3-Methy-1-butene | 0.0% | 0.0% | 0.1% | 0.0% | 0.1% | 0.0% | 0.0% | 0.4% |
| 2-Methy-1-butene | 0.0% | 0.0% | 0.2% | 0.0% | 0.2% | 0.0% | 0.0% | 1.9% |
| Sum of hexenes, hexanes, and heavier | 0.0% | 0.0% | 0.1% | 0.0% | 0.2% | 0.0% | 0.0% | 3.4% |
| Total mol % | 100.0% | 100.0% | 100.0% | 100.0% | 100.0% | 100.0% | 100.0% | 100.0% |

TABLE 8

| FIG. 2 with 80% efficiency in mol % | | | | | | | |
|---|---|---|---|---|---|---|---|
| Stream Number | 301A | 301E | 332 | 301F | 338 | 340 | 303A/B |
| Mole Flow, kmol/hr | 100.0 | 85.0 | 98.8 | 15.0 | 275.6 | 275.6 | 374.4 |
| Mass Flow, kg/hr | 5670 | 4819 | 4819 | 850 | 14943 | 14943 | 19762 |
| Volumn Flow m$^3$/hr | 6750 | 5737 | 6668 | 1012 | 4605 | 16513 | 31.5 |
| Enthalpy, MW | 0.6 | 0.5 | 0.9 | 0.1 | −4.0 | −0.3 | −6.0 |
| MW, g/mol | 56.7 | 56.7 | 48.8 | 56.7 | 54.2 | 54.2 | 52.8 |
| Density, kg/m$^3$ | 0.84 | 0.84 | 0.72 | 0.84 | 3.24 | 0.90 | 627.5 |
| COMPONENTS, mol % | | | | | | | |
| Ethylene | 0.0% | 0.0% | 15.1% | 0.0% | 10.3% | 6.1% | 8.5% |
| Propylene | 0.0% | 0.0% | 28.7% | 0.0% | 0.3% | 10.6% | 15.4% |
| Propane | 0.0% | 0.0% | 0.0% | 0.0% | 0.0% | 0.0% | 0.0% |
| 1-Butene | 0.0% | 0.0% | 3.1% | 0.0% | 3.8% | 3.2% | 3.2% |
| Isobutene | 0.0% | 0.0% | 6.5% | 0.0% | 22.8% | 19.2% | 15.8% |
| cis-2-butene | 35.4% | 35.4% | 9.2% | 35.4% | 7.3% | 3.9% | 5.3% |
| trans-2-butene | 35.4% | 35.4% | 9.8% | 35.4% | 8.7% | 4.7% | 6.0% |
| n-Butane | 29.3% | 29.3% | 25.2% | 29.3% | 50.3% | 50.3% | 43.7% |
| 1-Pentene | 0.0% | 0.0% | 0.1% | 0.0% | 0.0% | 0.0% | 0.0% |
| cis-2-Pentene | 0.0% | 0.0% | 0.2% | 0.0% | 0.0% | 0.6% | 0.5% |
| trans-2-Pentene | 0.0% | 0.0% | 0.3% | 0.0% | 0.1% | 1.3% | 1.0% |
| 2-Methyl-2-butene | 0.0% | 0.0% | 0.8% | 0.0% | 0.0% | 0.0% | 0.2% |
| 3-Methyl-1-butene | 0.0% | 0.0% | 0.1% | 0.0% | 0.0% | 0.0% | 0.0% |
| 2-Methyl-1-butene | 0.0% | 0.0% | 0.5% | 0.0% | 0.0% | 0.0% | 0.1% |
| Sum of hexenes, hexanes, and heavier | 0.0% | 0.0% | 0.5% | 0.0% | 0.0% | 0.1% | 0.1% |
| Total mol % | 100.0% | 100.0% | 100.0% | 100.0% | 100.0% | 100.0% | 100.0% |
| Stream Number | 336 | 334 | 306 | 307 | 308 | 316 | 312A/B | 314 |
| Mole Flow, kmol/hr | 3.2 | 28.6 | 342.6 | 57.1 | 285.5 | 25.8 | 232.1 | 27.7 |
| Mass Flow, kg/hr | 89 | 805 | 18868 | 2402 | 16466 | 1476 | 13288 | 1702 |
| Volumn Flow m$^3$/hr | 0.2 | 1.8 | 41.4 | 5.0 | 35.6 | 3.0 | 26.8 | 3.4 |
| Enthalpy, MW | 0.0 | 0.2 | −5.0 | 0.1 | −5.1 | −0.5 | −4.3 | −0.5 |
| MW, g/mol | 28.1 | 28.1 | 55.1 | 42.1 | 57.7 | 57.3 | 57.3 | 61.4 |
| Density, kg/m$^3$ | 438.1 | 438.1 | 455.3 | 477.4 | 462.5 | 496.7 | 496.7 | 500.3 |

TABLE 8-continued

FIG. 2 with 80% efficiency in mol %

| COMPONENTS, mol % | | | | | | | | |
|---|---|---|---|---|---|---|---|---|
| Ethylene | 99.3% | 99.3% | 0.0% | 0.3% | 0.0% | 0.0% | 0.0% | 0.0% |
| Propylene | 0.7% | 0.7% | 16.7% | 99.5% | 0.2% | 0.2% | 0.2% | 0.0% |
| Propane | 0.0% | 0.0% | 0.0% | 0.0% | 0.0% | 0.0% | 0.0% | 0.0% |
| 1-Butene | 0.0% | 0.0% | 3.5% | 0.0% | 4.1% | 4.6% | 4.6% | 0.4% |
| Isobutene | 0.0% | 0.0% | 17.3% | 0.2% | 20.7% | 22.8% | 22.8% | 1.4% |
| cis-2-butene | 0.0% | 0.0% | 5.8% | 0.0% | 6.9% | 6.4% | 6.4% | 11.8% |
| trans-2-butene | 0.0% | 0.0% | 6.6% | 0.0% | 7.9% | 8.0% | 8.0% | 6.9% |
| n-Butane | 0.0% | 0.0% | 47.7% | 0.0% | 57.3% | 57.9% | 57.9% | 51.7% |
| 1-Pentene | 0.0% | 0.0% | 0.0% | 0.0% | 0.1% | 0.0% | 0.0% | 0.5% |
| cis-2-Pentene | 0.0% | 0.0% | 0.6% | 0.0% | 0.7% | 0.0% | 0.0% | 6.7% |
| trans-2-Pentene | 0.0% | 0.0% | 1.1% | 0.0% | 1.3% | 0.1% | 0.1% | 13.1% |
| 2-Methyl-2-butene | 0.0% | 0.0% | 0.2% | 0.0% | 0.3% | 0.0% | 0.0% | 3.0% |
| 3-Methyl-1-butene | 0.0% | 0.0% | 0.0% | 0.0% | 0.1% | 0.0% | 0.0% | 0.4% |
| 2-Methyl-1-butene | 0.0% | 0.0% | 0.1% | 0.0% | 0.2% | 0.0% | 0.0% | 1.6% |
| Sum of hexenes, hexanes, and heavier | 0.0% | 0.0% | 0.1% | 0.0% | 0.1% | 0.0% | 0.0% | 2.4% |
| Total mol % | 100.0% | 100.0% | 100.0% | 100.0% | 100.0% | 100.0% | 100.0% | 100.0% |

Example 2

Table 17 shows butene conversion, propylene selectivity, and propylene yield for the embodiments of FIGS. 1 and 2. The data was determined using Aspen Plus® with the conditions as those provided for Tables 1 and 9.

The butene conversion is defined as:

$$\left(1 - \frac{\text{Mass flow of 2\_butene in combined reactor effluent}}{\text{Mass flow of 2\_butene in combined reactor feed}}\right) * 100\%$$

The propylene selectivity is defined as:

$$\left(\frac{\text{Mass flow of propylene in reactor effluent} - \text{Mass flow of propylene in reactor feed}}{\text{Mass flow of 2\_butene in reactor feed} * \text{butene conversion rate}}\right) * 100\%$$

The propylene yield is defined as:

$$\left(\frac{\text{Total Propylene Produced (wt. \%)}}{\text{Total 2\_butene in Feed (wt. \%)}}\right) * 100\%$$

TABLE 17

| | Embodiment of FIG. 1 | Embodiment of FIG. 2 |
|---|---|---|
| Butene Conversion | 80.6% | 79.9% |
| Propylene selectivity | 60.5% | 74.2% |
| Propylene yield | 79.8% | 69.6% |

For the purposes of describing and defining the present disclosure it is noted that the term "about" are utilized in this disclosure to represent the inherent degree of uncertainty that may be attributed to any quantitative comparison, value, measurement, or other representation. The term "about" are also utilized in this disclosure to represent the degree by which a quantitative representation may vary from a stated reference without resulting in a change in the basic function of the subject matter at issue. Additionally, the term "consisting essentially of" is used in this disclosure to refer to quantitative values that do not materially affect the basic and novel characteristic(s) of the disclosure. For example, a chemical stream "consisting essentially" of a particular chemical constituent or group of chemical constituents should be understood to mean that the stream includes at least about 99.5% of a that particular chemical constituent or group of chemical constituents.

It is noted that one or more of the following claims utilize the term "where" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

It should be understood that any two quantitative values assigned to a property may constitute a range of that property, and all combinations of ranges formed from all stated quantitative values of a given property are contemplated in this disclosure. It should be appreciated that compositional ranges of a chemical constituent in a stream or in a reactor should be appreciated as containing, in some embodiments, a mixture of isomers of that constituent. For example, a compositional range specifying butene may include a mixture of various isomers of butene. It should be appreciated that the examples supply compositional ranges for various streams, and that the total amount of isomers of a particular chemical composition can constitute a range.

Having described the subject matter of the present disclosure in detail and by reference to specific embodiments, it is noted that the various details described in this disclosure should not be taken to imply that these details relate to elements that are essential components of the various embodiments described in this disclosure, even in cases where a particular element is illustrated in each of the drawings that accompany the present description. Rather, the claims appended hereto should be taken as the sole representation of the breadth of the present disclosure and the corresponding scope of the various embodiments described in this disclosure. Further, it will be apparent that modifications and variations are possible without departing from the scope of the appended claims.

What is claimed is:

1. A process for producing propylene, the process comprising:
   at least partially metathesizing a first portion of a first stream to form a first metathesis-reaction product, the first stream comprising butene;
   at least partially cracking the first metathesis-reaction product to form a cracking-reaction product, the cracking reaction product comprising propylene and ethylene;
   at least partially separating ethylene from at least the cracking reaction product to form a first recycle stream, the first recycle stream comprising ethylene;
   combining the first recycle stream with a second portion of the first stream to a form a mixed stream; and
   at least partially metathesizing the mixed stream to form a second metathesis-reaction product, the second metathesis-reaction product comprising propylene.

2. The process of claim 1, where the first stream comprises at least 10 wt. % butene.

3. The process of claim 1, further comprising at least partially separating propylene from at least one of the cracking reaction product stream and the second metathesis-reaction product to form a product stream comprising at least 80 wt. % propylene.

4. The process of claim 1, further comprising at least partially separating butene from at least one of the cracking-reaction product and the second metathesis-reaction product to form a second recycle stream comprising at least 10 wt. % butene.

5. The process of claim 4, further comprising combining the second recycle stream with the first stream upstream of the first stream being partitioned into a first portion and a second portion.

6. The process of claim 4, further comprising combining the second recycle stream with second portion of the first stream.

7. The process of claim 1, where the first recycle stream comprises at least 80 wt. % ethylene.

8. The process of claim 1, where in the first cracking-reaction product and the second metathesis reaction product are mixed prior to one or more separation processes.

9. The process of claim 8, where the mixture of the first cracking-reaction product and the second metathesis reaction product comprises at least 10 wt. % propylene.

10. The process of claim 1, where the first portion of the first stream is metathesized with a metathesis catalyst and the first metathesis-reaction product is cracked with a cracking catalyst.

11. The process of claim 10, where the cracking catalyst is a mordenite framework inverted (MFI) structured silica catalyst.

12. The process of claim 10, where the metathesis catalyst is a mesoporous silica catalyst impregnated with metal oxide.

13. A process for producing propylene, the process comprising:
   introducing a first portion of a first stream comprising butene to a first reactor, where the first reactor comprises a first metathesis catalyst and a cracking catalyst, the first metathesis catalyst positioned generally upstream of the cracking catalyst;
   at least partially metathesizing the first portion of the first stream with the first metathesis catalyst to form a first metathesis-reaction product;
   at least partially cracking the first metathesis-reaction product with the cracking catalyst to produce a cracking-reaction product comprising propylene and ethylene;
   passing the cracking-reaction product out of the first reactor in a cracking-reaction product stream;
   combining a first recycle stream with a second portion of the first stream to a form a mixed stream and introducing the mixed stream to a second reactor, the second reactor comprising a second metathesis catalyst;
   at least partially metathesizing the mixed stream with the second metathesis catalyst in the second reactor to produce a second metathesis-reaction product comprising propylene and passing the second metathesis-reaction product out of the second reactor in a second metathesis-reaction product stream;
   at least partially separating ethylene from the cracking-reaction product stream, the second metathesis-reaction product stream, or a stream comprising a mixture of both, to form the first recycle stream; and
   at least partially separating propylene from the cracking-reaction product stream, second metathesis-reaction product stream, or a stream comprising a mixture of both, to form a product stream comprising propylene.

14. The process of claim 13, where the first stream comprises at least 10 wt. % butene.

15. The process of claim 13, where in the cracking-reaction product and the second metathesis reaction product are mixed prior to one or more separation processes.

16. The process of claim 15, where the mixture of the first cracking-reaction product and the second metathesis reaction product comprises at least 10 wt. % propylene.

17. The process of claim 13, where a ratio of the mass flowrate of the first portion of the first stream and the second portion of the first stream is from 1:1 to 6:1.

18. The process of claim 13, further comprising at least partially separating butene from at least one of the cracking-reaction product stream and the second metathesis-reaction product stream to form a second recycle stream comprising at least 10 wt. % butene.

19. A process for producing propylene, the process comprising:
   introducing a first portion of a first stream comprising butene to a first reactor, where the first reactor comprises a first metathesis catalyst;
   at least partially metathesizing the first portion of the first stream with the first metathesis catalyst to form a first metathesis-reaction product;
   passing the first metathesis-reaction product to a second reactor, where the first reactor comprises a cracking catalyst;
   at least partially cracking the first metathesis-reaction product with the cracking catalyst to produce a cracking-reaction product comprising propylene and ethylene;
   passing the cracking-reaction product out of the second reactor in a cracking-reaction product stream;
   combining an ethylene recycle stream with a second portion of the first stream comprising butene to a form a mixed stream and introducing the mixed stream to a third reactor, the third reactor comprising a second metathesis catalyst;

at least partially metathesizing the mixed stream with the second metathesis catalyst in the third reactor to produce a second metathesis-reaction product comprising propylene and passing the second metathesis-reaction product out of the third reactor in a second metathesis-reaction product stream;

at least partially separating ethylene from the cracking-reaction product stream, the second metathesis-reaction product stream, or a stream comprising a mixture of both, to form the ethylene recycle stream; and at least partially separating propylene from the cracking-reaction product stream, the second metathesis-reaction product stream, or a stream comprising a mixture of both, to form a product stream comprising propylene.

20. The process of claim 19, where the first stream comprises at least 10 wt. % butene.

21. The process of claim 19, where the cracking-reaction product and the second metathesis reaction product are mixed prior to one or more separation processes.

22. The process of claim 21, where the mixture of the cracking-reaction product and the second metathesis-reaction product comprises at least 10 wt. % propylene.

23. The process of claim 19, further comprising at least partially separating butene from at least one of the cracking-reaction product stream and the second metathesis-reaction product stream to form a system recycle second comprising at least 10 wt. % butene.

* * * * *

UNITED STATES PATENT AND TRADEMARK OFFICE
CERTIFICATE OF CORRECTION

PATENT NO. : 9,834,497 B2  
APPLICATION NO. : 15/191009  
DATED : December 5, 2017  
INVENTOR(S) : Sohel Shaikh, Aqil Jamal and Zhonglin Zhang Page 1 of 1

It is certified that error appears in the above-identified patent and that said Letters Patent is hereby corrected as shown below:

On the Title Page

Item (57), Abstract:
"stream with a second portion of the first stream to a form a mixed stream, and at least partially metathesizing the mixed stream to from a second metathesis-reaction product. In"
Should read:
--stream with a second portion of the first stream to form a mixed stream, and at least partially metathesizing the mixed stream to form a second metathesis-reaction product. In--; and In the Claims Column 31, Line 23, Claim 1:
"of the first stream to a form a mixed stream; and"
Should read:
--of the first stream to form a mixed stream; and--; and Column 32, Line 14, Claim 13:
"the first stream to a form a mixed stream and introducing"
Should read:
--the first stream to form a mixed stream and introducing--; and Column 32, Line 65, Claim 19:
"portion of the first stream comprising butene to a form"
Should read:
--portion of the first stream comprising butene to form--; and Column 33, Line 29, Claim 23:
"product stream to form a system recycle second comprising"
Should read:
--product stream to form a system recycle stream comprising--.

Signed and Sealed this  
Eighth Day of January, 2019

Andrei Iancu  
*Director of the United States Patent and Trademark Office*